(12) United States Patent
Ziraldo et al.

(10) Patent No.: US 12,416,102 B2
(45) Date of Patent: Sep. 16, 2025

(54) SYSTEMS AND METHODS FOR TRANSFER OF REAGENTS BETWEEN DROPLETS

(71) Applicant: 10X Genomics, Inc., Pleasanton, CA (US)

(72) Inventors: Solongo B. Ziraldo, Pleasanton, CA (US); Geoffrey McDermott, Livermore, CA (US); Shea Thompson Lance, Livermore, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 1034 days.

(21) Appl. No.: 17/397,775

(22) Filed: Aug. 9, 2021

(65) Prior Publication Data

US 2022/0025438 A1 Jan. 27, 2022

Related U.S. Application Data

(63) Continuation of application No. PCT/US2020/017785, filed on Feb. 11, 2020.

(60) Provisional application No. 62/934,256, filed on Nov. 12, 2019, provisional application No. 62/804,633, filed on Feb. 12, 2019.

(51) Int. Cl.
*C40B 50/06* (2006.01)
(52) U.S. Cl.
CPC .................................. *C40B 50/06* (2013.01)
(58) Field of Classification Search
None
See application file for complete search history.

(56) References Cited

U.S. PATENT DOCUMENTS

| 4,124,638 A | 11/1978 | Hansen |
| 5,185,099 A | 2/1993 | Delpuech et al. |
| 5,270,183 A | 12/1993 | Corbett et al. |
| 5,478,893 A | 12/1995 | Ghosh et al. |
| 5,736,330 A | 4/1998 | Fulton |
| 5,756,334 A | 5/1998 | Perler et al. |
| 5,846,719 A | 12/1998 | Brenner et al. |

(Continued)

FOREIGN PATENT DOCUMENTS

| EP | 1019496 B1 | 9/2004 |
| EP | 1841879 A2 | 10/2007 |

(Continued)

OTHER PUBLICATIONS

Co-pending U.S. Appl. No. 18/152,650, inventor Shastry; Shankar, filed Jan. 10, 2023.

(Continued)

*Primary Examiner* — Christian C Boesen
(74) *Attorney, Agent, or Firm* — WILSON SONSINI GOODRICH & ROSATI

(57) ABSTRACT

The disclosure provides systems and methods for droplet processing. For example, a method can include providing a first droplet and a second droplet. In some cases, the first droplet may have a first concentration of a reagent and the second droplet may have a second concentration of the reagent. The second droplet may comprise a bead or a biological particle. The method can also include subjecting the first droplet and the second droplet to conditions sufficient to transfer the reagent from the first droplet to the second droplet, thereby decreasing the first concentration in the first droplet and increasing the second concentration in the second droplet.

21 Claims, 19 Drawing Sheets

(56) References Cited

U.S. PATENT DOCUMENTS

| | | |
|---|---|---|
| 5,900,481 A | 5/1999 | Lough et al. |
| 5,942,609 A | 8/1999 | Hunkapiller et al. |
| 5,994,056 A | 11/1999 | Higuchi |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |
| 6,176,962 B1 | 1/2001 | Soane et al. |
| 6,306,590 B1 | 10/2001 | Mehta et al. |
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,915,679 B2 | 7/2005 | Chien et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,544,473 B2 | 6/2009 | Brenner |
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,592,150 B2 | 11/2013 | Drmanac et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,764,322 B2 | 9/2017 | Hiddessen et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,557,158 B2 | 2/2020 | Hardenbol et al. |
| 10,590,244 B2 | 3/2020 | Delaney et al. |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,995,333 B2 | 5/2021 | Pfeiffer |
| 11,371,094 B2 | 6/2022 | Ryvkin et al. |
| 11,459,607 B1 | 10/2022 | Terry et al. |
| 11,467,153 B2 | 10/2022 | Belhocine et al. |
| 11,596,908 B2 | 3/2023 | Link et al. |
| 11,655,499 B1 | 5/2023 | Pfeiffer |
| 11,845,983 B1 | 12/2023 | Belhocine et al. |
| 11,851,683 B1 | 12/2023 | Maheshwari et al. |
| 11,851,700 B1 | 12/2023 | Bava et al. |
| 11,920,183 B2 | 3/2024 | Bharadwaj et al. |
| 11,952,626 B2 | 4/2024 | Pfeiffer et al. |
| 12,065,688 B2 | 8/2024 | Bell |
| 12,084,715 B1 | 9/2024 | Lund |
| 12,163,179 B2 | 12/2024 | Bell et al. |
| 12,169,198 B2 | 12/2024 | Price et al. |
| 12,188,014 B1 | 1/2025 | Price et al. |
| 12,235,262 B1 | 2/2025 | Giresi |
| 2002/0005354 A1 | 1/2002 | Spence et al. |
| 2002/0051971 A1 | 5/2002 | Stuelpnagel et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0215862 A1 | 11/2003 | Parce et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |

(56) References Cited

U.S. PATENT DOCUMENTS

| | | |
|---|---|---|
| 2008/0004436 A1 | 1/2008 | Tawfik et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0305761 A1 | 12/2011 | Shum et al. |
| 2012/0071331 A1 | 3/2012 | Casbon et al. |
| 2012/0172259 A1 | 7/2012 | Rigatti et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2014/0065234 A1 | 3/2014 | Shum et al. |
| 2014/0155295 A1 | 6/2014 | Hindson et al. |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0034163 A1 | 2/2015 | Abate et al. |
| 2015/0267191 A1 | 9/2015 | Steelman et al. |
| 2015/0361418 A1 | 12/2015 | Reed |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0080075 A1 | 3/2018 | Brenner et al. |
| 2018/0105808 A1 | 4/2018 | Mikkelsen et al. |
| 2018/0312822 A1 | 11/2018 | Lee et al. |
| 2018/0312873 A1 | 11/2018 | Zheng |
| 2018/0340169 A1 | 11/2018 | Belhocine et al. |
| 2018/0356430 A1 | 12/2018 | Thiam et al. |
| 2018/0371545 A1 | 12/2018 | Wong et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0127731 A1 | 5/2019 | McDermott |
| 2019/0134633 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2020/0005902 A1 | 1/2020 | Mellen et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0261879 A1 | 8/2020 | Abate et al. |
| 2020/0263232 A1 | 8/2020 | Bell et al. |
| 2020/0291454 A1 | 9/2020 | Belhocine et al. |
| 2020/0407775 A1 | 12/2020 | Bharadwaj et al. |
| 2021/0190770 A1 | 6/2021 | Delaney et al. |
| 2021/0270703 A1 | 9/2021 | Abousoud |
| 2024/0002914 A1 | 1/2024 | Pfeiffer et al. |
| 2024/0272044 A1 | 8/2024 | Bava |
| 2025/0051847 A1 | 2/2025 | Ziraldo et al. |
| 2025/0075272 A1 | 3/2025 | Ziraldo et al. |

FOREIGN PATENT DOCUMENTS

| | | |
|---|---|---|
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-95/30782 | 11/1995 |
| WO | WO-99/52708 | 10/1999 |
| WO | WO-2000008212 A1 | 2/2000 |
| WO | WO-2001002850 A1 | 1/2001 |
| WO | WO-0114589 A2 | 3/2001 |
| WO | WO-0190418 A1 | 11/2001 |
| WO | WO--2001089787 A2 | 11/2001 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005021151 A1 | 3/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009152928 A2 | 12/2009 |
| WO | WO-2010033200 A2 | 3/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |

(56) References Cited

FOREIGN PATENT DOCUMENTS

| | | |
|---|---|---|
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2014028378 A2 | 2/2014 |
| WO | WO-2014108810 A2 | 7/2014 |
| WO | WO-2014165559 A2 | 10/2014 |
| WO | WO-2015015199 A2 | 2/2015 |
| WO | WO-2015044428 A1 | 4/2015 |
| WO | WO-2015164212 A1 | 10/2015 |
| WO | WO-2016040476 A1 | 3/2016 |
| WO | WO-2016061517 A2 | 4/2016 |
| WO | WO-2016126871 A2 | 8/2016 |
| WO | WO-2016145409 A1 | 9/2016 |
| WO | WO-2016168584 A1 | 10/2016 |
| WO | WO-2017015075 A1 | 1/2017 |
| WO | WO-2017066231 A1 | 4/2017 |
| WO | WO-2017180949 A1 | 10/2017 |
| WO | WO-2017184707 A1 | 10/2017 |
| WO | WO-2017197343 A2 | 11/2017 |
| WO | WO-2018039338 A1 | 3/2018 |
| WO | WO-2018091676 A1 | 5/2018 |
| WO | WO-2018119301 A1 | 6/2018 |
| WO | WO-2018119447 A2 | 6/2018 |
| WO | WO-2018156935 A1 | 8/2018 |
| WO | WO-2018172726 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020167862 A1 | 8/2020 |
| WO | WO-2020167866 A1 | 8/2020 |
| WO | WO-2020168013 A1 | 8/2020 |
| WO | WO-2020198532 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2024243444 A1 | 11/2024 |

OTHER PUBLICATIONS

Co-pending U.S. Appl. No. 18/392,684, inventors Fernandes; Sunjay Jude et al., filed Dec. 21, 2023.

Co-pending U.S. Appl. No. 18/743,583, inventor Nagendran; Monica, filed Jun. 14, 2024.

Co-pending U.S. Appl. No. 18/795,976, inventors Meer; Elliott et al., filed Aug. 6, 2024.

Co-pending U.S. Appl. No. 18/824,258, inventor Stott; Ryan Timothy, filed Sep. 4, 2024.

Co-pending U.S. Appl. No. 18/959,351, inventor Schnalll-Levin; Michael, filed Nov. 25, 2024.

Co-pending U.S. Appl. No. 19/044,383, inventors Smibert; Peter et al., filed Feb. 3, 2025.

Co-pending U.S. Appl. No. 19/093,986, inventors Bloju; Octavian Marian et al., filed Mar. 28, 2025.

Gruner et al., Controlling molecular transport in minimal emulsions, Nature Communications vol. 7, Article No. 10392, Published: Jan. 22, 2016.

Johnson, Mary, Detergents: Triton X-100, Tween-20, and More, Labome, Material Methods, 3:163-175 (2013) retrieved online Jan. 31, 2025.

Schuch et al., Formation and Fluorimetric Characterization of Micelles in a Micro-flow Through System with Static Micro Mixer. Sensors, 7(11); 2499-2509 (2007).

10X Genomics, Inc. CG000153 Rev A. Chromium Single Cell DNA Reagent Kits User Guide. 2018.

10X Genomics, Inc. CG000184 Rev A. Chromium Single Cell 3' Reagent Kits v3 User Guide with Feature Barcoding Technology for CRISPR Screening. 2018.

10X Genomics, Inc. CG000185 Rev B. Chromium Single Cell 3' Reagent Kits User Guide with Feature Barcoding Technology for Cell Surface Protein. 2018.

10X Genomics, Inc. CG000208 Rev E. Chromium Next GEM Single Cell V(D)J reagent Kits v1.1 User Guide with Feature Barcode Technology for Cell Surface Protein. 2020.

10X Genomics, Inc. CG000209 Rev D. Chromium Next GEM Single Cell ATAC Reagent Kits v1.1 User Guide. 2020.

10X Genomics, Inc. CG000239 Rev B. Visium Spatial Gene Expression Reagent Kits User Guide. 2020.

10X Genomics, Inc. CG00026. Chromium Single Cell 3' Reagent Kit User Guide. 2016.

10X Genomics, Inc. LIT00003 Rev B Chromium Genome Solution Application Note. 2017.

Abate, A.R. et al. "Beating Poisson encapsulation statistics using close-packed ordering" Lab on a Chip (Sep. 21, 2009) 9(18):2628-2631.

Adamson et al., "Production of arrays of chemically distinct nanolitre plugs via repeated splitting in microfluidic devices", Lab Chip 6(9): 1178-1186 (Sep. 2006).

Agasti, S.S. et al. "Photocleavable DNA barcode-antibody conjugates allow sensitive and multiplexed protein analysis in single cell" J Am Chem Soc (2012) 134(45):18499-18502.

Amini, S. et al. "Haplotype-resolved whole-genome sequencing by contiguity-preserving transposition and combinatorial indexing" Nature Genetics (2014) 46:1343-1349 doi:10.1038/ng.3119.

Anna et al.: Formation of dispersions using "flow focusing" in microchannels: Applied Physics Letters, vol. 82, No. 3, pp. 364-366 (2003).

Baret, "Surfactants in droplet-based microfluidics" Lab Chip (12(3):422-433 (2012).

Beer et al. On-Chip, Real-Time, Single-Copy Polymerase Chain Reaction in Picoliter Droplets. Anal Chem 79:8471-8475 (2007).

Braeckmans et al., Scanning the Code. Modern Drug Discovery. 2003:28-32.

(56) References Cited

OTHER PUBLICATIONS

Brenner, et al. "In vitro cloning of complex mixtures of DNA on microbeads: physical separation of differentially expressed cDNAs." Proc Natl Acad Sci U S A. Feb. 15, 2000;97(4):1665-70.

Buchman GW, et al. Selective RNA amplification: a novel method using dUMP-containing primers and uracil DNA glycosylase. PCR Methods Appl. Aug. 1993; 3(1):28-31.

Burns, et al. An Integrated Nanoliter DNA Analysis Device. Science. Oct. 16, 1998;282(5388):484-7.

Burns, et al. Microfabricated structures for integrated DNA analysis. Proc Natl Acad Sci U S A. May 28, 1996; 93(11): 5556-5561.

Burns, et al. The intensification of rapid reactions in multiphase systems using slug flow in capillaries. Lab Chip. Sep. 2001;1(1):10-15. Epub Aug. 9, 2001.

Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.

Chien et al. "Multiport flow-control system for lab-on-a-chip microfluidic devices", Fresenius J. Anal Chem, 371:106-111 (Jul. 27, 2001).

Chu, et al. Controllable monodisperse multiple emulsions. Angew Chem Int Ed Engl. 2007;46(47):8970-4.

Clausell-Tormos et al., "Droplet-based microfluidic platforms for the encapsulation and screening of mammalian cells and multicellular organisms", Chem. Biol. 15:427-437 (2008).

Co-pending U.S. Appl. No. 16/434,076, inventor Giresi; Paul, filed Jun. 6, 2019.

Co-pending U.S. Appl. No. 16/434,084, inventor Giresi; Paul, filed Jun. 6, 2019.

Co-pending U.S. Appl. No. 16/434,102, inventors Price; Andrew D. et al., filed Jun. 6, 2019.

Co-pending U.S. Appl. No. 16/737,762, inventors Price; Andrew D. et al., filed Jan. 8, 2020.

Co-pending U.S. Appl. No. 16/737,770, inventors Belhocine; Zahara Kamila et al., filed Jan. 8, 2020.

Co-pending U.S. Appl. No. 16/789,273, inventors Maheshwari; Arundhati Shamoni et al., filed Feb. 12, 2020.

Co-pending U.S. Appl. No. 16/800,450, inventor Katherine; Pfeiffer, filed Feb. 25, 2020.

Co-pending U.S. Appl. No. 17/014,909, inventor Giresi; Paul, filed Sep. 8, 2020.

Co-pending U.S. Appl. No. 17/148,942, inventors McDermott; Geoffrey et al., filed Jan. 14, 2021.

Co-pending U.S. Appl. No. 17/166,982, inventors McDermott; Geoffrey et al., filed Feb. 3, 2021.

Co-pending U.S. Appl. No. 17/175,542, inventors Maheshwari; Arundhati Shamoni et al., filed Feb. 12, 2021.

Co-pending U.S. Appl. No. 17/220,303, inventor Walter; Dagmar, filed Apr. 1, 2021.

Co-pending U.S. Appl. No. 17/318,364, inventors Bava; Felice Alessio et al., filed May 12, 2021.

Co-pending U.S. Appl. No. 17/381,612, inventor Martinez; Luigi Jhon Alvarado, filed Jul. 21, 2021.

Co-pending U.S. Appl. No. 17/499,039, inventors Pfeiffer; Katherine et al., filed Oct. 12, 2021.

Co-pending U.S. Appl. No. 17/512,241, inventors Hill; Andrew John et al., filed Oct. 27, 2021.

Co-pending U.S. Appl. No. 17/517,408, inventors Salmanzadeh; Alireza et al., filed Nov. 2, 2021.

Co-pending U.S. Appl. No. 17/518,213, inventor Lund; Paul Eugene, filed Nov. 3, 2021.

Co-pending U.S. Appl. No. 17/522,741, inventors Zheng; Xinying et al., filed Nov. 9, 2021.

Co-pending U.S. Appl. No. 17/545,862, inventor Katherine; Pfeiffer, filed Dec. 8, 2021.

Co-pending U.S. Appl. No. 17/573,350, inventor Corey; M. Nemec, filed Jan. 11, 2022.

Co-pending U.S. Appl. No. 17/580,947, inventor Gibbons; Michael, filed Jan. 21, 2022.

Co-pending U.S. Appl. No. 17/831,835, inventor Martinez; Luigi Jhon Alvarado, filed Jun. 3, 2022.

Co-pending U.S. Appl. No. 17/957,781, inventor Bava; Felice Alessio, filed Sep. 30, 2022.

Co-pending U.S. Appl. No. 18/046,843, inventor Toh; Mckenzi, filed Oct. 14, 2022.

Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.

Drmanac et al., Sequencing by hybridization (SBH): advantages, achievements, and opportunities. Adv Biochem Eng Biotechnol. 2002;77 :75-101.

Duffy et al., Rapid Protyping of Microfluidic Systems and Polydimethylsiloxane, Anal Chem 70:4974-4984 (1998).

Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.

Esser-Kahn, et al. Triggered release from polymer capsules. Macromolecules. 2011; 44:5539-5553.

Gericke, et al. Functional cellulose beads: preparation, characterization, and applications. Chemical reviews 113.7 (2013): 4812-4836.

Guo, et al. Droplet microfluidics for high-throughput biological assays. Lab Chip. Jun. 21, 2012;12(12):2146-55. doi: 10.1039/c2lc21147e. Epub Feb. 9, 2012.

Gyarmati, et al. Reversible disulphide formation in polymer networks: a versatile functional group from synthesis to applications. European Polymer Journal. 2013; 49:1268-1286.

Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.

Holtze, et al. Biocompatible surfactants for water-in-fluorocarbon emulsions. Lab Chip. Oct. 2008;8(10):1632-9. doi: 10.1039/b806706f. Epub Sep. 2, 2008.

Hug, et al. Measurement of the number of molecules of a single mRNA species in a complex mRNA preparation. J Theor Biol. Apr. 21, 2003;221(4):615-24.

Islam, et al. Highly multiplexed and strand-specific single-cell RNA 5' end sequencing. Nat Protoc. Apr. 5, 2012;7(5):813-28. doi: 10.1038/nprot.2012.022.

Jaitin, et al. Massively parallel single-cell RNA-seq for marker-free decomposition of tissues into cell types. Science. Feb. 14, 2014;343(6172):776-9. doi: 10.1126/science.1247651.

Jarosz, M. et al. "Using 1ng of DNA to detect haplotype phasing and gene fusions from whole exome sequencing of cancer cell lines" Cancer Res (2015) 75(supp15):4742.

Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.

Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.

Kenis, et al. Microfabrication Inside Capillaries Using Multiphase Laminar Flow Patterning. Science. 1999; 285:83-85.

Kivioja, et al. Counting absolute numbers of molecules using unique molecular identifiers. Nat Methods. Nov. 20, 2011;9(1):72-4.

Klein, et al. Droplet barcoding for single-cell transcriptomics applied to embryonic stem cells. Cell. May 21, 2015; 161:1187-1201.

Korlach et al., Methods in Enzymology, Real-Time DNA Sequencing from Single Polymerase Molecules, (2010) 472:431-455.

Koster et al., "Drop-based microfluidic devices for encapsulation of single cells", Lab on a Chip The Royal Soc. of Chem. 8: 1110-1115 (2008).

Lagally, et al. Single-Molecular DNA Amplification and Analysis in an Integrated Microfluidic Device. Anal Chem. Feb. 1, 2001;73(3):565-70.

Lennon et al. A scalable, fully automated process for construction of sequence-ready barcoded libraries for 454. Genome Biology 11:R15 (2010).

(56) References Cited

OTHER PUBLICATIONS

MacOsko, et al. Highly Parallel Genome-wide Expression Profiling of Individual Cells Using Nanoliter Droplets. Cell. May 21, 2015;161(5):1202-14. doi: 10.1016/j.cell.2015.05.002.
Madl, et al. "Bioorthogonal Strategies for Engineering Extracellular matrices", Madal, Chritopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10):1346-54. Epub Jul. 31, 2006.
McCoy, R et al. "Illumina TruSeq Synthetic Long-Reads Empower De Novo Assembly and Resolve Complex, Highly-Repetitive Transposable Elements" PLOS (2014) 9(9):e1016689.
Microfluidic ChipShop. Microfluidic product catalogue. Oct. 2009.
Navin. The first five years of single-cell cancer genomics and beyond. Genome Res. Oct. 2015;25(10):1499-507. doi: 10.1101/gr.191098.115.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, R. et al., "Single cell multiplex gene detection and sequencing using microfluidicallygenerated agarose emulsions" Angew. Chem. Int. Ed. Engl. (2011) 50(2):390-395.
Orakdogen, N. "Novel responsive poly(N,N-dimethylaminoethyl methacrylate) gel beads: preparation, mechanical properties and pH-dependent swelling behavior" J Polym Res (2012) 19:9914.
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Priest, et al. Generation of Monodisperse Gel Emulsions in a Microfluidic Device, Applied Physics Letters, 88:024106 (2006).
Pushkarev et al. "Single-molecule sequencing of an individual human genome," Nature Biotech (2009) 27:847-850.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL: http://454.com/downloads/my454/documentation/technical-bulletins/TCB-09004 UsingMultiplexIdentifierAdaptorsForTheGSFLXTitaniumSeriesChemistry-BasicMIDSet.pdf.
Rotem, A. et al., "High-throughput single-cell labeling (Hi-SCL) for RNA-Seq using drop-based microfluidics" PLOS One (May 22, 2015) 0116328 (14 pages).
Saikia, et al. Simultaneous multiplexed amplicon sequencing and transcriptome profiling in single cells. Nat Methods. Jan. 2019; 16(1):59-62. doi: 10.1038/s41592-018-0259-9. Epub Dec. 17, 2018.

Schlicht et al., "Droplet-interface-bilayer assays in microfluidic passive networks", Scientific Reports, vol. 5, Apr. 24, 2015 (Apr. 24, 2015), p. 9951, XP055260973,DOI: 10.1038/srep09951.
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors. Polymer. vol. 51, Issue 25, Nov. 26, 2010, pp. 5883-5889.
Seiffert, S. et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1)107-121.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Uttamapinant, et al. Fast, cell-compatible click chemistry with copper-chelating azides for biomolecular labeling. Angew. Chem. Int. End. Engl., Jun. 11, 2012: 51(24) pp. 5852-5856.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.
Zhang, et al. One-step fabrication of supramolecular microcapsules from microfluidic droplets. Science. Feb. 10, 2012;335(6069):690-4. doi: 10.1126/science.1215416.
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu, et al. Reverse transcriptase template switching: a SMART approach for full-length cDNA library construction. Biotechniques. Apr. 2001;30(4):892-7.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.

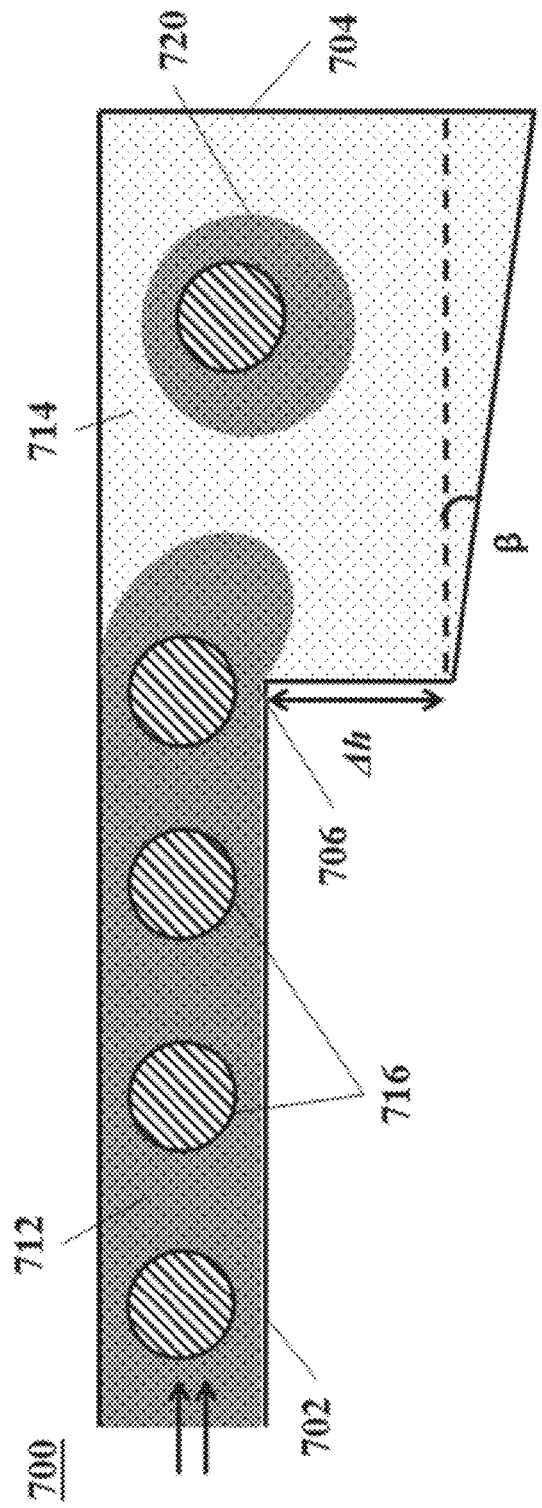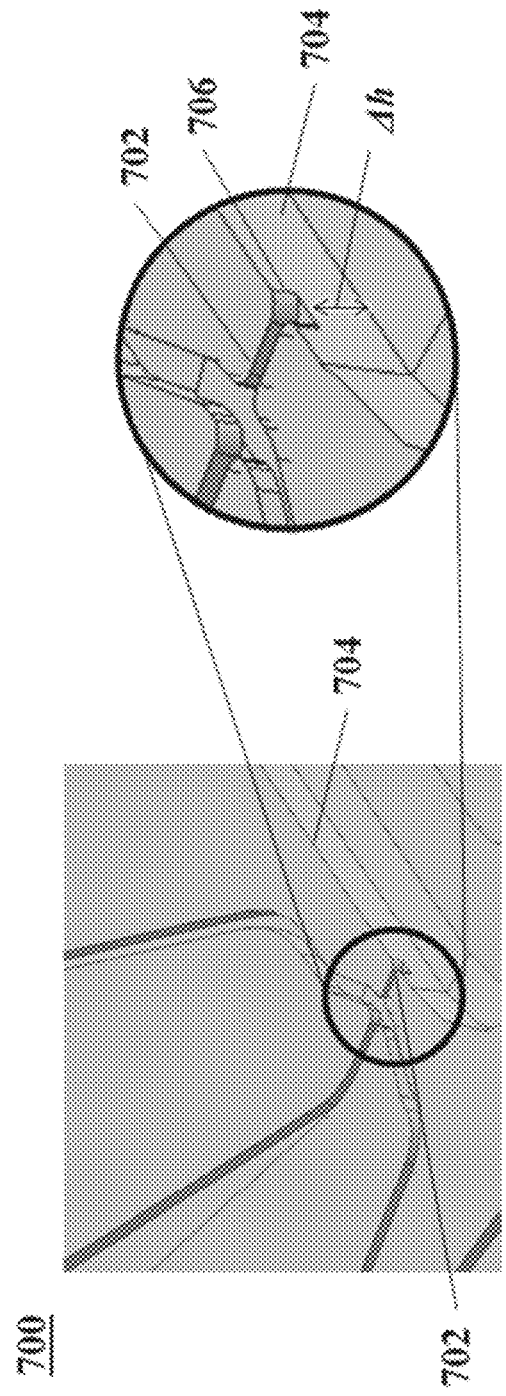
FIG. 7A
FIG. 7B

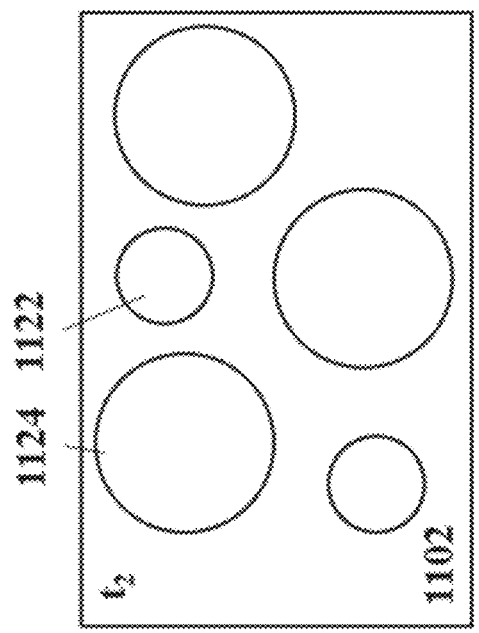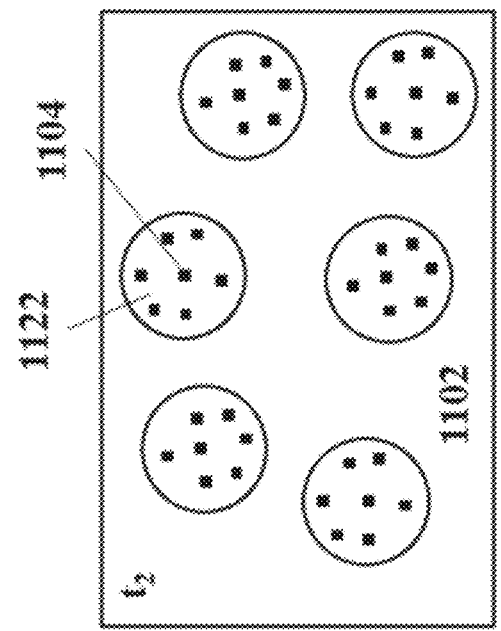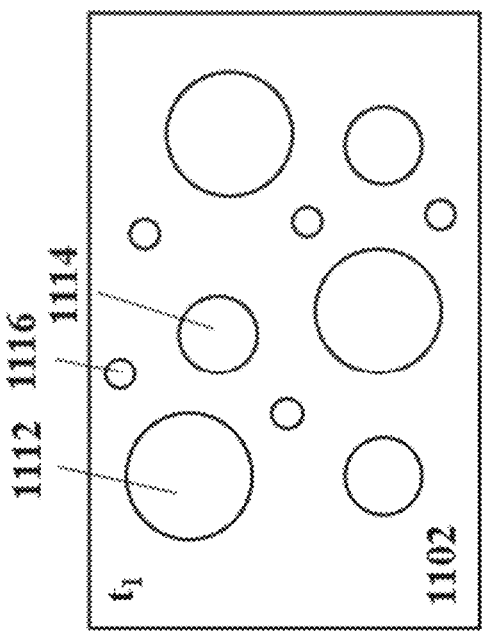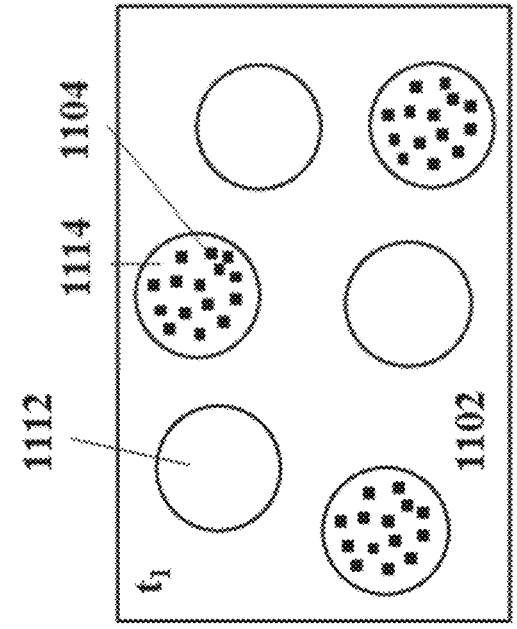
FIG. 11A
FIG. 11B

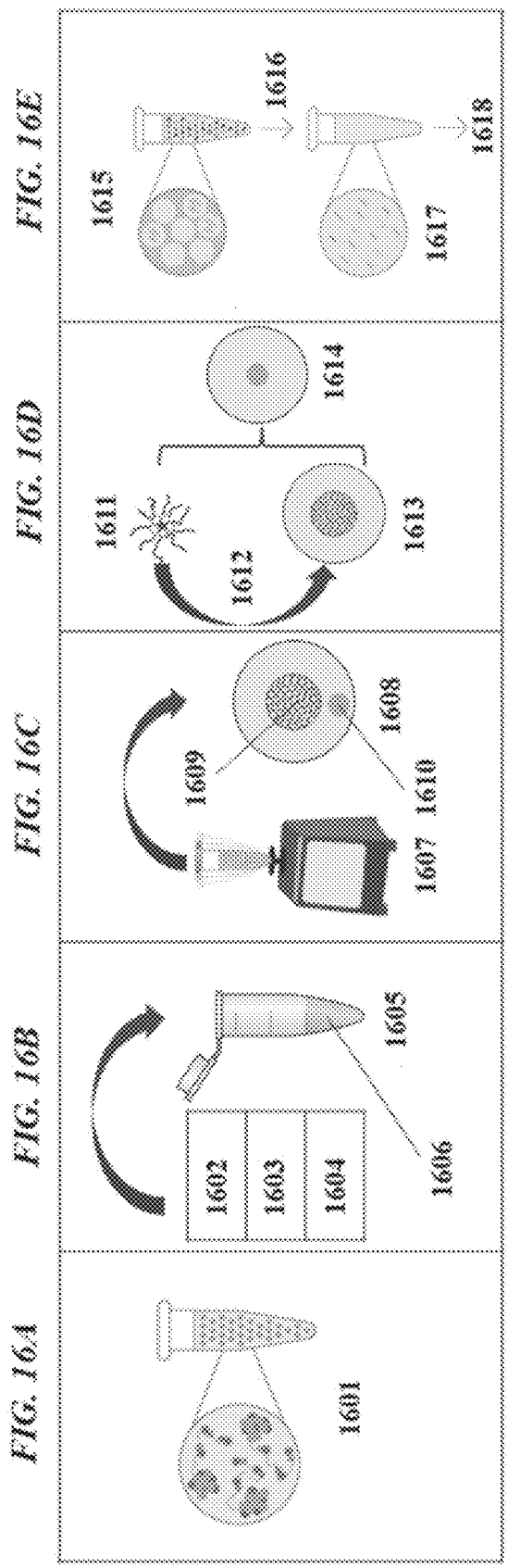

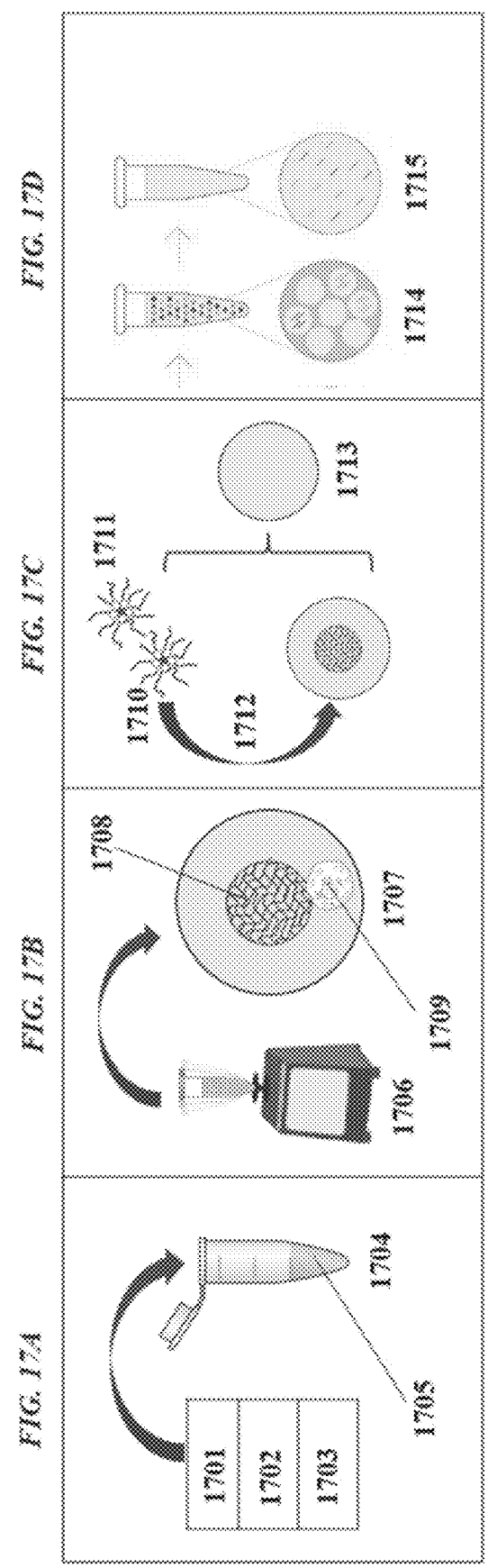

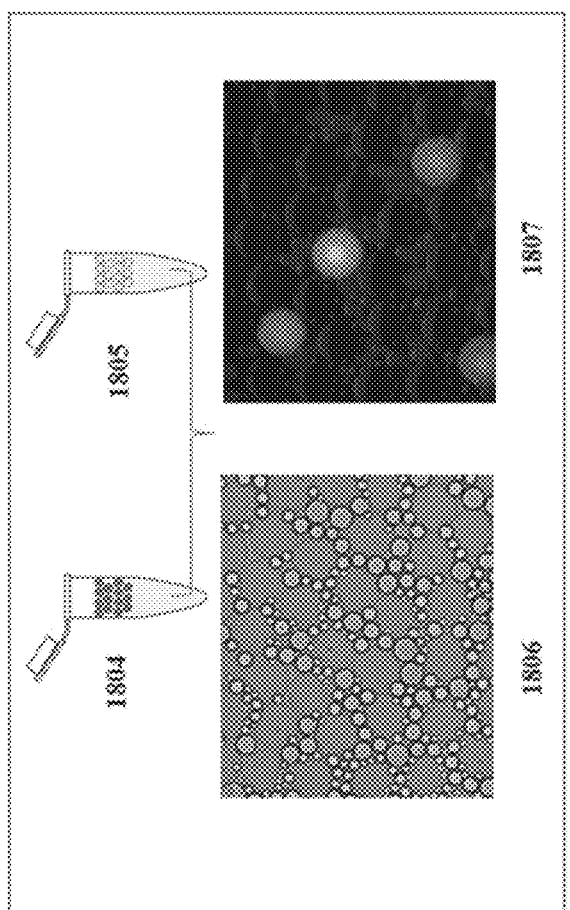
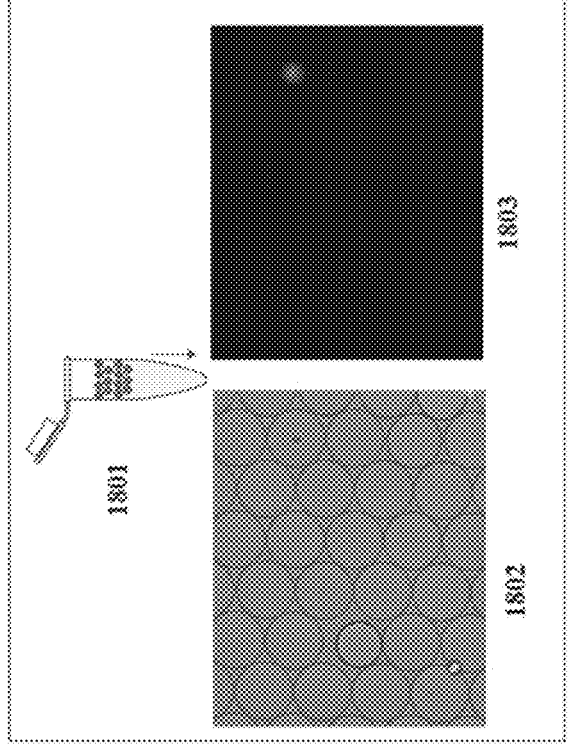

SYSTEMS AND METHODS FOR TRANSFER OF REAGENTS BETWEEN DROPLETS

CROSS-REFERENCE

This application is a continuation of International Application No. PCT/US2020/017785, filed Feb. 11, 2020, which claims the benefit of U.S. Provisional Patent Application No. 62/934,256, filed Nov. 12, 2019, and U.S. Provisional Patent Application No. 62/804,633, filed Feb. 12, 2019, each of which is entirely incorporated herein by reference.

BACKGROUND

A sample may be processed for various purposes, such as identification of a type of moiety within the sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

Partitioning reagents in droplets can be useful for analyzing various samples.

SUMMARY

Changing an amount of reagent in a droplet, such as increasing or decreasing the concentration, remains challenging. In an example, an amount or reagent in a droplet may be changed in order to affect the rate or progress of a reaction within the droplet. Such reactions may include cleaving or formation of a bond, reduction, oxidation, hydrolysis, etc. Accordingly, recognized herein is a need for improved systems and methods for processing droplets. In particular, systems and methods described herein are useful in controlling the rate or progress of a reaction inside of a droplet.

An aspect of the present disclosure provides a method for droplet processing. The comprises: (a) providing a first droplet population and a second droplet population, wherein droplets from the first droplet population have a first concentration of a reagent and droplets from the second droplet population have a second concentration of the reagent, and wherein the droplets from the second droplet population comprise a bead or an analyte carrier; and (b) subjecting the first droplet population and the second droplet population to conditions sufficient to transfer the reagent between the first droplet population and the second droplet population, thereby changing the first concentration of the reagent in the first droplet population and the second concentration of the reagent in the second droplet population.

In some embodiments, in (a), the reagent is absent from the second droplet population.

In some embodiments, the reagent is selected from the group consisting of a reducing agent, lysis agent, sodium ion (Na+), magnesium ion (Mg2+), potassium ion (K+), ammonium ion (NH4+), chloride (Cl—), bromide (Br—), iodide (I—), fluoride (F—), adenosine triphosphate (ATP), dinucleotide triphosphate (dNTP), dimethyl sulfoxide (DMSO), dimethylformamide (DMF), and n-dodecyl-beta-D-maltoside (DBDM). In some embodiments, wherein the reducing agent is dithiothreitol or a functional derivative thereof.

In some embodiments, the first droplet population comprises a first droplet fraction and a first fluid fraction and wherein the second droplet population comprises a second droplet fraction and a second fluid fraction. In some embodiments, the first fluid fraction or the second fluid fraction comprises a mediator that aids in transfer of the reagent between the first droplet population and the second droplet population. In some embodiments, in (b), the reagent is transferred between the first droplet population and the second droplet population via the mediator. In some embodiments, the mediator is derived from the first droplet population. In some embodiments, the mediator comprises a surfactant. In some embodiments, the mediator is a micelle.

In some embodiments, (b) comprises subjecting the first droplet population to conditions sufficient to transfer the reagent from the first droplet fraction to the first fluid fraction and subjecting the second droplet population to conditions sufficient to transfer the reagent from the first fluid fraction to droplets of the second droplet population. In some embodiments, the first fluid fraction is a continuous phase in which the first droplet population is dispersed. In some embodiments, wherein the continuous phase comprises an oil. In some embodiments, the first droplet population is provided in a first container and the second droplet population is provided in a second container, and wherein (b) further comprises transferring the first fluid fraction of the first droplet population from the first container to the second container.

In some embodiments, the method further comprises, subsequent to (a), generating a mixture comprising the first droplet population and the second droplet population, wherein the reagent is between the first droplet population and the second droplet population within the mixture. In some embodiments, the reagent is transferred between the first droplet population and the second droplet population within the mixture via diffusion.

In some embodiments, the bead has nucleic acid molecules coupled thereto. In some embodiments, the nucleic acid molecules are nucleic acid barcode molecules. In some embodiments, the reagent dissolves the bead or releases at least a portion of the nucleic acid molecules from the bead.

In some embodiments, the bead is a gel bead. In some embodiments, the reagent dissolves the gel bead.

In some embodiments, the reagent is a reducing agent and the bead comprises a disulfide bond that is broken by the reducing agent.

In some embodiments, the analyte carrier is a cell. In some embodiments, the reagent lyses the cell. In some embodiments, the analyte carrier is a cell bead.

In some embodiments, the droplets from the second droplet population comprise the bead and the analyte carrier.

In some embodiments, in (a), the first concentration is greater than the second concentration.

In some embodiments, the droplets from the second droplet population comprise an antibody coupled to a nucleic acid molecule. In some embodiments, the reagent is capable of breaking a linkage between the antibody and the nucleic acid molecule.

In some embodiments, during or subsequent to (b), the droplets from the first droplet population decrease in size or the droplets from the second droplet population increase in size.

In some embodiments, prior to (a), the droplets from the first droplet population or the droplets from the second droplet population are generated using a microfluidic device.

In some embodiments, prior to (a), the first droplet population or the second droplet population is generated upon agitation of a mixture of immiscible phases.

In some embodiments, the method further comprises prior to (a), generating the second droplet population from (i) a first fluid volume comprising a population of beads and a population of analyte carriers and (ii) a second fluid volume immiscible with the first fluid volume, wherein a droplet from the second droplet population comprises the bead from the population of beads and the analyte carrier from the population of analyte carriers.

In some embodiments, the second droplet population is generated by applying energy to the first fluid volume, the second fluid volume, or both the first fluid volume and the second fluid volume. In some embodiments, the second droplet population is generated by providing a mixture comprising the first fluid volume and the second fluid volume and agitating the mixture.

In some embodiments, the second droplet population is generated in absence of using a microfluidic device. In some embodiments, the second droplet population is generated using a microfluidic device. In some embodiments, the first fluid volume comprises an aqueous fluid. In some embodiments, the second fluid volume comprises an oil. In some embodiments, the first fluid volume does not include the reagent.

In some embodiments, the droplet comprises a single bead and a single analyte carrier. In some embodiments, the analyte carrier is a cell. In some embodiments, the analyte carrier is a cell bead. In some embodiments, the analyte carrier is a cell nucleus. In some embodiments, the population of analyte carriers comprises a plurality of transposed nuclei.

In some embodiments, the method further comprises subjecting a population of cell nuclei to transposition in bulk to yield the plurality of transposed nuclei. In some embodiments, the method further comprises subsequent to (b), using a nucleic acid molecule derived from the analyte carrier and a nucleic acid barcode molecule coupled to the bead to generate a barcoded nucleic acid molecule. In some embodiments, the method further comprises sequencing the barcoded nucleic acid molecule, or derivative thereof.

In an aspect, the present disclosure provides a method for nucleic acid processing, comprising: (a) agitating (i) a first fluid volume comprising a population of beads and a population of analyte carriers, wherein the population of beads comprises a plurality of nucleic acid barcode molecules, wherein the population of analyte carriers comprises a plurality of nucleic acid molecules, and (ii) a second fluid volume immiscible with the first fluid volume, to generate a plurality of droplets, wherein a first droplet from the plurality of droplets comprises a bead from the population of beads and an analyte carrier from the population of analyte carriers, wherein the bead comprises a nucleic acid barcode molecule of the plurality of nucleic acid barcode molecules, wherein the analyte carrier comprises a nucleic acid molecule of the plurality of nucleic acid molecules, wherein the first droplet has a first concentration of a reagent, and wherein the reagent is configured to release the nucleic acid barcode molecule or release the nucleic acid molecule in the droplet; (b) subjecting the first droplet and a second droplet having a second concentration of the reagent to conditions sufficient to transfer the reagent between the first droplet and the second droplet, thereby changing the first concentration of the reagent in the first droplet and the second concentration of the reagent in the second droplet; and (c) generating a barcoded nucleic acid molecule using at least the nucleic acid barcode molecule and the nucleic acid molecule in the first droplet. In some embodiments, agitating comprises vortexing.

In some embodiments, the first fluid volume comprises an aqueous fluid. In some embodiments, the second fluid volume comprises an oil. In some embodiments, the first fluid volume does not include the reagent. In some embodiments, the first droplet comprises a single bead and a single analyte carrier. In some embodiments, the analyte carrier is a cell. In some embodiments, the reagent lyses the cell. In some embodiments, the analyte carrier is a cell bead. In some embodiments, the analyte carrier is a cell nucleus.

In some embodiments, the plurality analyte carriers comprise a plurality of transposed nuclei. In some embodiments, the method further comprises subjecting a population of cell nuclei to transposition in bulk to yield the plurality of transposed nuclei. In some embodiments, the method further comprises sequencing the barcoded nucleic acid molecule, or derivative thereof.

In some embodiments, the reagent is selected from the group consisting of a reducing agent, lysis agent, sodium ion (Na+), magnesium ion (Mg2+), potassium ion (K+), ammonium ion (NH4+), chloride (Cl—), bromide (Br—), iodide (I—), fluoride (F—), adenosine triphosphate (ATP), dinucleotide triphosphate (dNTP), dimethyl sulfoxide (DMSO), dimethylformamide (DMF), and n-dodecyl-beta-D-maltoside (DBDM). In some embodiments, the reducing agent is dithiothreitol or a functional derivative thereof.

In some embodiments, the plurality of droplets is provided in a first droplet fraction and a first fluid fraction, wherein (b) comprises providing a second plurality of droplets in a second droplet fraction and a second fluid fraction. In some embodiments, the first fluid fraction or the second fluid fraction comprises a mediator that aids in transfer of the reagent between the first droplet and the second droplet.

In some embodiments, in (b), the reagent is transferred between the first droplet and the second droplet via the mediator. In some embodiments, the mediator comprises a surfactant. In some embodiments, the mediator is a micelle.

In some embodiments, (b) comprises subjecting the second plurality of droplets to conditions sufficient to transfer the reagent from the second droplet fraction to the second fluid fraction and subjecting the plurality of droplets to conditions sufficient to transfer the reagent from the first fluid fraction to the first droplet fraction. In some embodiments, the first fluid fraction is a continuous phase in which the plurality of droplets is dispersed. In some embodiments, the continuous phase comprises an oil.

In some embodiments, the method further comprises, in (b), generating a mixture comprising the plurality of droplets and the second plurality of droplets, wherein the reagent is between the plurality of droplets and the second plurality of droplets within the mixture. In some embodiments, the reagent is transferred between the first droplet and the second droplet within the mixture via diffusion. In some embodiments, the bead has a subset of nucleic acid barcode molecules of the plurality of nucleic acid barcode molecules coupled thereto.

In some embodiments, the reagent dissolves the bead or releases at least a portion of the subset of nucleic acid barcode molecules from the bead. In some embodiments, the bead is a gel bead. In some embodiments, the reagent dissolves the gel bead. In some embodiments, the reagent is a reducing agent and the bead comprises a disulfide bond that is broken by the reducing agent.

In some embodiments, prior to (b), the first concentration is less than the second concentration. In some embodiments, during or subsequent to (b), the second droplet decreases in diameter or the first droplet increases in diameter.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 7A shows a cross-section view of another example of a microfluidic channel structure with a geometric feature for controlled partitioning;

FIG. 7B shows a perspective view of the channel structure of FIG. 7A;

FIG. 11A and FIG. 11B show two additional example modes of transferring a reagent between droplets;

FIGS. 16A through 16E show an example sample processing workflow comprising droplet generation with the aid of agitation, as described in Example 3.

FIGS. 17A through 17D show an example gene expression workflow comprising droplet generation with the aid of agitation, as described in Example 4.

FIGS. 18A and 18B show the results of an experiment comprising transporting a reagent after droplet generation and lysing the encapsulated cells, as described in Example 5.

DETAILED DESCRIPTION

Figure 1:
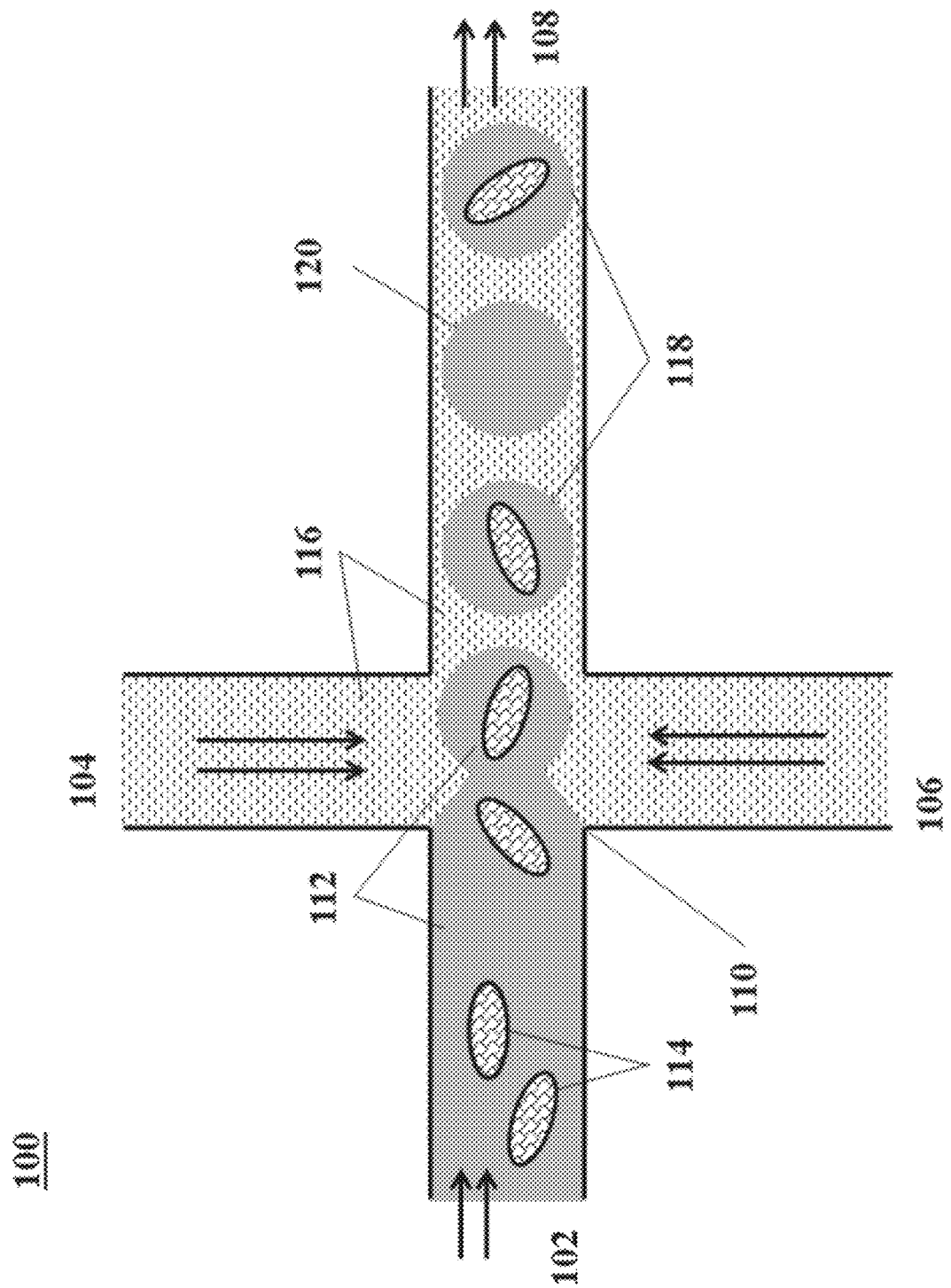
FIG. 1 shows an example of a microfluidic channel structure for partitioning individual analyte carriers.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The terms "a," "an," and "the," as used herein, generally refers to singular and plural references unless the context clearly dictates otherwise.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values.

For example, less than or equal to 3, 2, or 1 is equivalent to less than or equal to 3, less than or equal to 2, or less than or equal to 1.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

As used herein, the term "barcoded nucleic acid molecule" generally refers to a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence or a non-targeted sequence. For example, in the methods and systems described herein, hybridization and reverse transcription of a nucleic acid molecule (e.g., a messenger RNA (mRNA) molecule) of a cell with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the mRNA.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "analyte carrier," as used herein, generally refers to a discrete biological system derived from a biological sample. The analyte carrier may be or comprise a biological particle. The analyte carrier may be a macromolecule. The analyte carrier may be a small molecule. The analyte carrier may be a virus. The analyte carrier may be a cell or derivative of a cell. The analyte carrier may be an organelle. The analyte carrier may be a rare cell from a population of cells. The analyte carrier may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The analyte carrier may be a constituent of a cell. The analyte carrier may be or may include DNA, RNA, organelles, proteins, or any combination thereof. The analyte carrier may be or may include a matrix (e.g., a gel or polymer matrix) comprising a cell or one or more constituents from a cell (e.g., cell bead), such as DNA, RNA, organelles, proteins, or any combination thereof, from the cell. The analyte carrier may be obtained from a tissue of a subject. analyte carrier may be a hardened cell. Such hardened cell may or may not include a cell wall or cell membrane. In some cases, the analyte carrier may include one or more constituents of a cell but may not include other constituents of the cell. An example of such constituents is a nucleus or an organelle. A cell may be a live cell. The live cell may be capable of being cultured, for example, being cultured when enclosed in a gel or polymer matrix or cultured when comprising a gel or polymer matrix.

The term "macromolecular constituent," as used herein, generally refers to a macromolecule contained within or from an analyte carrier or biological particle. The macromolecular constituent may comprise a nucleic acid. In some cases, the analyte carrier may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

Droplet Processing

Provided herein are systems and methods for processing a droplet. A droplet can be processed such that an amount of a reagent within a droplet may be changed. An amount of reagent within a droplet may be changed by using the principles of mass transport. In an example, an amount of reagent may be changed through differences in the distribution of droplet sizes, for example, Otswald ripening. In another example, the amount of reagent within a droplet may be changed through heterogeneities in chemical potential between droplets of different reagent compositions, for example, osmosis-driven transport. In another example, the amount or reagent within a droplet may be changed through solubilization of a reagent in an assembly or surfactant molecules, for example, a micelle, which may act as a carrier or mediator of one or more reagents between droplets.

The present disclosure provides a method for droplet processing. The method may comprise: providing a first droplet and a second droplet, such that the first droplet may have a first concentration of a reagent, and the second droplet may have a second concentration of the reagent. Further, the second droplet may comprise a bead and/or an analyte carrier. In some examples, an analyte carrier may comprise or be a biological particle, such as a cell or part of a cell, a biochemical entity such as a protein, peptide, or other molecule, or other types of analyte carriers, such as analyte carriers provided elsewhere herein. The method may further comprise subjecting the first droplet and the second droplet to conditions sufficient to transfer the reagent from the first droplet to the second droplet, which may decrease the first concentration in the first droplet and increase the second concentration in the second droplet. In some cases, the second droplet may comprise the bead and the analyte carrier. In some examples, the first droplet is part of a first droplet population and/or the second droplet is part of a second droplet population. In other examples, one or more droplets from the first droplet population comprise a reagent at a first concentration and one or more droplets from the second droplet population comprise the same reagent at a second concentration. In one example, the method includes providing the first and second droplet populations with conditions sufficient to transfer the reagent between the first and second droplet populations which may change the first concentration in the first droplet population and the second concentration in the second droplet population. In another example, the conditions are sufficient to transfer the reagent from one or more droplets of the first droplet population to one or more droplets of the second droplet population which may decrease the first concentration of the reagent in the first droplet population and increase the second concentration of the reagent in the second droplet population. In other examples, the second droplet or second droplet population are initially provided such that the reagent is absent from the second droplet or second droplet population. In another example, the second droplet or second droplet population as initially provided comprise a bead and/or an analyte carrier.

The first droplet and the second droplet are examples of types of partitions as described elsewhere herein. For example, the droplet may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A droplet may comprise one or more other (inner) partitions. In some cases, an inner partition may also generally be referred to herein as a core, or a core droplet. An outer partition, such as the area of the droplet outside the inner partition (e.g., core) may also generally be referred to herein as a shell. In some cases, different partitions of a droplet may comprise different phases. In some examples, the inner partition (e.g., core) may comprise a gel or bead. In some examples, the outer partition (e.g., shell) may comprise an aqueous solution comprising reagents and/or analyte carriers, or vice versa. A droplet may comprise several layers or partitions. For example, a droplet may comprise a core and multiple shells. Each droplet layer or partition may be generated using the methods described herein. A combination of droplet generation methods may be used.

The bead may comprise a bead as described elsewhere herein. In some cases, the bead may be a gel bead as described elsewhere herein. In some cases, the bead may be a cell bead as described elsewhere. The analyte carrier may comprise a biological particle as described elsewhere herein. In some cases, the analyte carrier may comprise a cell as described elsewhere. In some cases, the analyte carrier may be a cell bead.

The bead may comprise nucleic acid molecules coupled thereto. The nucleic acid molecules may be nucleic acid barcode molecules. In some cases, the bead may comprise a plurality of nucleic acid barcode molecules. The plurality of nucleic acid barcode molecules comprises at least about 1,000 nucleic acid barcode molecules, at least about 5,000 nucleic acid barcode molecules, at least about 10,000 nucleic acid barcode molecules, at least about 50,000 nucleic acid barcode molecules, at least about 100,000 nucleic acid barcode molecules, at least about 500,000 nucleic acid barcode molecules, at least about 1,000,000 nucleic acid barcode molecules, at least about 5,000,000 nucleic acid barcode molecules, at least about 10,000,000 nucleic acid barcode molecules, at least about 100,000,000 nucleic acid barcode molecules, at least about 1,000,000,000 nucleic acid barcode molecules, or more. In some cases, the nucleic acid cell molecules comprise the same barcode sequence. As described elsewhere herein, a nucleic acid barcode sequence can be used to identify a cell for which species (e.g., cell nucleic acids, cell surface features) have been identified with nucleic acid molecules that have been barcoded with nucleic acid barcode sequences.

The reagent may be a reducing agent. For example, the reducing agent may be dithiothreitol (DTT) or a functional derivative thereof. For example, the reducing agent may be DTT, TCEP, etc. The reagent may dissolve the gel bead. The reagent may be a reducing agent and the bead may comprise a disulfide that is broken by the reducing agent. The reagent may dissolve the bead or may release at least a portion of the nucleic acid molecules from the bead.

In some cases, the reagent may be one or more of an oxidizing agent, an acid (e.g. a Lewis acid, a proton donor, etc.), a base (e.g. a Lewis base, a proton acceptor, etc.), a complexing agent, water, an enzyme, a protein, a ligand, one or more nucleic acid components, an oligonucleotide, a biochemical signaling agent, etc. Moreover, the reagent may be any small molecule or macromolecule, which may participate in a reaction with the bead, species associated with the bead and/or the analyte carrier. The reagent may comprise a salt or an ion thereof (e.g.: sodium ion (Na+), magnesium ion (Mg2+), potassium ion (K+), ammonium ion (NH4+), chloride (Cl—), bromide (Br—), iodide (I—), (F—), etc). The reagent may comprise any molecule and/or solvent used in biochemical reactions (e.g. adenosine triphosphate (ATP), dinucleotidetriphosphates (dNTPs), dimethylsulfoxide (DMSO), dimethylformamide (DMF), etc.). The reagent may comprise any of the other reagents disclosed herein elsewhere.

The first droplet may comprise a reagent at a concentration of at least about 1 nanoMolar (nM), 2 nM, 5 nM, 10 nM, 20 nM, 50 nM, 100 nM, 200 nM, 500 nM, 1 microMolar (μM), 2 μM, 5 μM, 10 μM, 20 μM, 50 μM, 100 μM, 200 μM, 500 μM, 1 mM (milliMolar), 2 mM, 5 mM, 10 mM, 20 mM, 50 mM, 100 mM, 200 mM, 500 mM, 1 M (Molar), or more. The first droplet may comprise a reagent at a concentration of at most about 1 nM, 2 nM, 5 nM, 10 nM, 20 nM, 50 nM, 100 nM, 200 nM, 500 nM, 1 μM, 2 μM, 5 μM, 10 μM, 20 μM, 50 μM, 100 μM, 200 μM, 500 μM, 1 mM (milliMolar), 2 mM, 5 mM, 10 mM, 20 mM, 50 mM, 100 mM, 200 mM, 500 mM, 1 M (Molar), 2 M, 3 M, 4 M, 5 M, 6 M, 7 M, 8 M, 9 M, 10 M, 50 M, 100 M or more.

The second droplet may comprise a reagent at a concentration of at least about 1 nM, 2 nM, 5 nM, 10 nM, 20 nM, 50 nM, 100 nM, 200 nM, 500 nM, 1 μM, 2 μM, 5 μM, 10 μM, 20 M, 50 μM, 100 μM, 200 μM, 500 μM, 1 mM (milliMolar), 2 mM, 5 mM, 10 mM, 20 mM, 50 mM, 100 mM, 200 mM, 500 mM, 1 M (Molar), or more. The second droplet may comprise a reagent at a concentration of at most about 1 nM, 2 nM, 5 nM, 10 nM, 20 nM, 50 nM, 100 nM, 200 nM, 500 nM, 1 μM, 2 μM, 5 μM, 10 μM, 20 μM, 50 μM, 100 μM, 200 μM, 500 μM, 1 mM (milliMolar), 2 mM, 5 mM, 10 mM, 20 mM, 50 mM, 100 mM, 200 mM, 500 mM, 1 M (Molar), 2 M, 3 M, 4 M, 5 M, 6 M, 7 M, 8 M, 9 M, 10 M, 50 M, 100 M or more. In some cases, the second droplet may not contain the reagent. A case where the second droplet does not contain the reagent the reagent may be at a concentration of less than or equal to 1 nM, 100 picoMolar (pM), 10 pM, 1 pM, 100 femtoMolar, or less.

In some cases, the first concentration of the reagent in the first droplet is greater than the second concentration of the reagent in the second droplet. However, in some cases, the first concentration and the second concentration may be substantially the same to within at least about 1%, 2%, 5%, 10%, 20%, or more. In other cases, the second concentration of the reagent in the second droplet is greater than the first concentration of the reagent in the first droplet.

A method of processing a droplet may further comprise, prior to providing a first and a second droplet, generating the first droplet or the second droplet with the aid of a microfluidic device or with the aid of agitation of a mixture of immiscible phases. For example, microfluidic channel networks (e.g., on a chip) can be utilized to generate droplets as described herein. For example, the first droplet and the second droplet may comprise droplets in an emulsion as described elsewhere herein. The first droplet and the second droplet may comprise droplets in a colloid. In some cases, the emulsion may comprise a microemulsion or a nanoemulsion.

The first droplet and the second droplet may be formed by creating an emulsion by mixing or agitating immiscible phases. Mixing or agitation may comprise various agitation techniques, such as vortexing, pipetting, tube flicking, or other agitation techniques. In some cases, mixing or agitation may be performed without using a microfluidic device. In some examples, the first droplet and the second droplet may be formed by exposing a mixture to ultrasound or sonication.

In some cases, a combination of droplet generation techniques may be used. For example, droplets may comprise an inner partition (a core) and an outer partition (a shell). The core droplet (the inner droplet) can be generated with the aid of a microfluidic device while the shell droplet (the outer droplet) may be generated with the aid of agitation of the mixture comprising the core droplets, or vice versa. Alternatively, both the core and the shell droplets may be generated using an agitation technique, or both the core and the shell droplets may be generated using a microfluidic device.

The first and the second droplet may comprise droplets in a medium, such as an emulsion or colloid. The medium may comprise a fluid which may comprise different physical properties than a fluid within a droplet, such as solubility, miscibility, viscosity, phase, etc. In an example, the fluid inside the droplet comprises an aqueous solution and the medium comprises an oil. The medium may comprise a continuous phase of an emulsion. In cases in which the medium comprises a continuous phase of an emulsion, the continuous phase may comprise an oil. In some cases, the medium may comprise a fluid which is a continuous phase in which the first droplet is dispersed. In some cases, the medium may comprise a fluid which is a continuous phase in which the second droplet is dispersed. In some cases, the fluid can comprise an oil, such as fluorinated oil, that includes a fluorosurfactant for stabilizing droplets, for example, inhibiting subsequent coalescence of the resulting droplets. In some cases, however, droplets can be prepared such that they can be fused or merged.

The medium comprising the droplet may comprise a fractionation. For example, one fraction of the medium may comprise a greater number of droplets than another fraction. In another example, the medium may comprise an oil fraction, which comprises predominately oil but may comprise some droplets. The medium may comprise an aqueous fraction, which comprises predominately water but may comprise some droplets. The medium may comprise a plurality of fractions which may differ by, for example, phase transition, droplet concentration, miscibility of various types of fluids, viscosity, solubility, etc.

Figure 10:
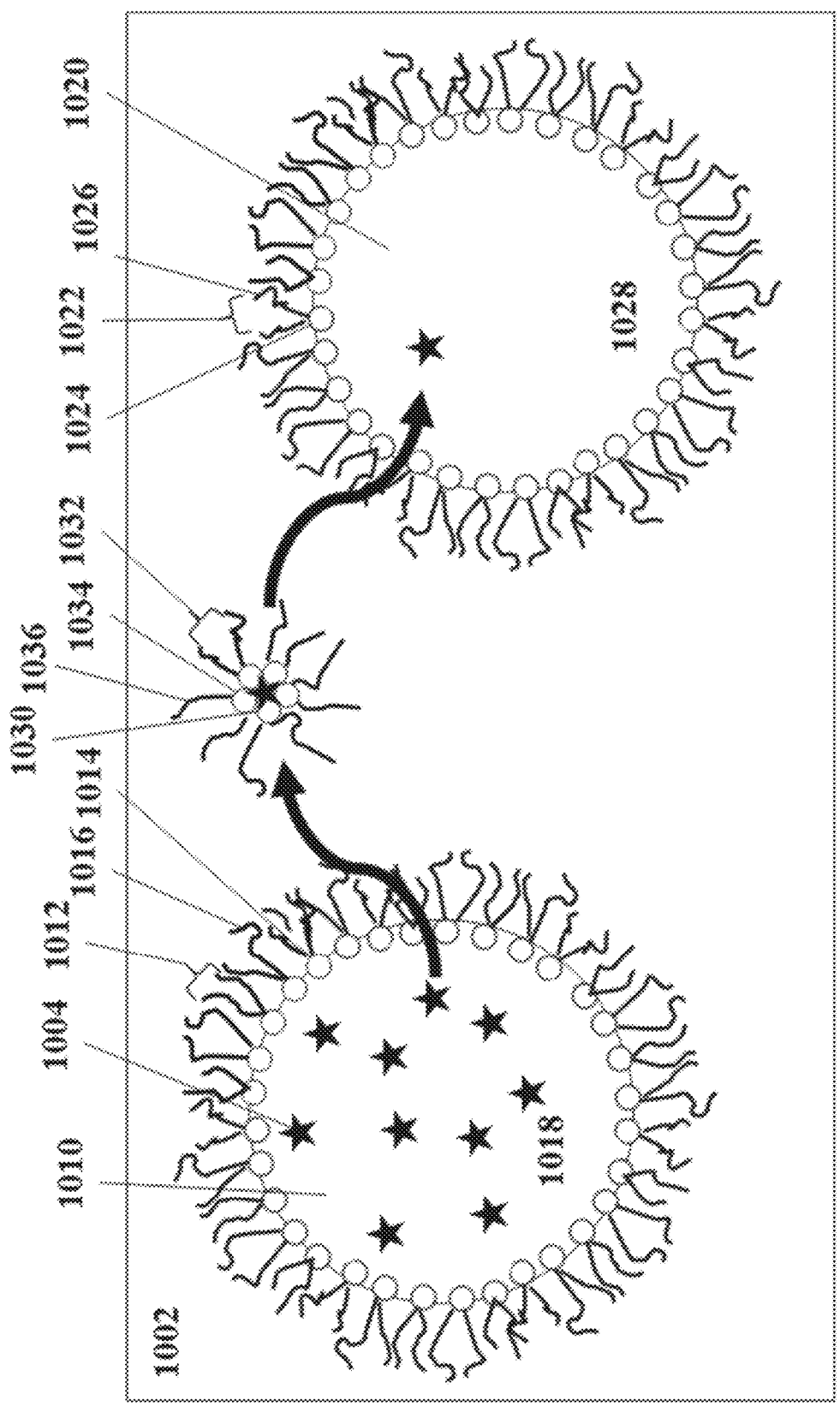
FIG. 10 shows an example mode of transferring a reagent from a first droplet to a second droplet using a mediator.

In some cases, the method further comprises subjecting the first droplet to conditions sufficient to transfer the reagent out of the first droplet and into a fluid. In some cases, the method may comprise subsequently providing conditions sufficient to transfer the reagent from the fluid into the second droplet. FIG. 10, FIG. 11A, and FIG. 11B show example modes of transferring a reagent from a first droplet into a fluid and, subsequently, from fluid into a second droplet. In some cases, providing conditions sufficient to transfer the reagent out of the first droplet and into the second droplet comprises a mode of transferring a reagent from a first droplet to a second droplet.

FIG. 10 shows an example mode of transferring a reagent from a first droplet to a second droplet using a mediator. As shown, the medium 1002 may comprise a first droplet 1010, a second droplet 1020, and a mediator 1030. In the illustrated example, a reagent 1004 is indicated with stars. As shown, first droplet 1010 may comprise a surfactant 1012 comprising a surfactant head 1014 and a surfactant tail 1016. The interior of first droplet 1010 may comprise a fluid 1018. The fluid 1018 may comprise a fluid with different physical properties than the medium 1002 such as viscosity, density, composition, and/or other properties such as with respect to each other (e.g., solubility, miscibility, etc.). The fluid 1018 in the interior of the droplet (e.g., aqueous phase) may be substantially immiscible and/or substantially insoluble in the fluid medium (e.g., organic or oil phase). Alternatively, in some cases, the fluid 1018 in the interior of the droplet (e.g., aqueous phase) may be partially soluble in the fluid medium 1002. In some cases, it may be preferred to minimize the solubility of the fluid 1028 in the fluid medium 1002. In some cases, the fluid 1018 is an aqueous phase. Fluid 1018 may comprise a first concentration of reagent 1004. As shown, second droplet 1020 may comprise a surfactant 1022 comprising a surfactant head 1024 and a surfactant tail 1026, which surfactant 1022 may be the same as surfactant 1012. The interior of second droplet 1020 may comprise a fluid 1028. In some cases, the fluid 1028 is an aqueous phase. The fluid 1028 may comprise a fluid with different physical properties than the medium 1002, such as density, viscosity, composition and/or other properties such as with respect to each other (e.g., solubility, miscibility, etc.). The fluid 1018 in the interior of the droplet (e.g., aqueous phase) may be substantially immiscible and/or substantially insoluble in the fluid medium 1002 (e.g., organic or oil phase). Alternatively, in some cases, the fluid 1018 in the interior of the droplet (e.g., aqueous phase) may be partially soluble in the fluid medium 1002. In some cases, it may be preferred to minimize the solubility of the fluid 1028 in the fluid medium 1002. Fluid 1028 may comprise a first concentration of reagent 1004. In some cases, the reagent may be transferred from the first droplet to the second droplet using a mediator derived from the first droplet. In some cases, the mediator accepts the reagent from the first droplet, for example, via diffusion or by budding of a mediator from the first droplet. The mediator comprising the reagent may then transfer the reagent from the mediator to the second droplet. The mediator may be absorbed by the second droplet. The reagent may diffuse from the mediator to the second droplet.

In some examples, the mediator is a droplet component that is configured to transfer a reagent from the droplet containing the mediator away from the droplet. In another example, the transfer of the reagent comprises a transfer away from a first droplet to a second droplet. In one example, prior to the transfer of the reagent away from the first droplet, the reagent is absent from second droplet. The first droplet may be part of a first droplet population and the second droplet may be part of a second droplet population.

As shown in FIG. 10, the mediator 1030 may be a micelle. In another example, the mediator may comprise a liposome.

The mediator may comprise a molecular assembly, which may aid in the transport of a reagent. The molecular assembly may comprise a "cage" of molecules around the reagent. The mediator may comprise a surfactant 1032 comprising a surfactant head 1034 and a surfactant tail 1036, which may be the same surfactant as surfactant 1012 and/or 1022. The surfactant may comprise a molecule with a head and a tail which comprise different solubility. The surfactant head may be more soluble in a fluid in the interior of the micelle, and the surfactant tail may be more soluble in medium 1002. In an example, the solubility of the head may be greater in water and a tail may be more soluble in the oil. A mediator surfactant may comprise the same surfactant as the first and/or the second droplet. The mediator may be formed from the first of the second droplet. A micelle may comprise an aggregate of surfactant molecules dispersed in a fluid. The micelle or liposome may be spherical, may comprise ellipsoids, may be cylindrical, may be bilayers, etc. The size and shape of the micelle may be changed by adjusting surfactant and/or fluid conditions such as pH, temperature, surfactant concentration in the fluid, solute concentration in the fluid, reagent concentration in the fluid, ionic strength of the fluid, etc.

FIG. 11A and FIG. 11B show two additional example modes of transferring a reagent from a first droplet to a second droplet, which may underlie transfer using mediators as in FIG. 10. In a first example shown in FIG. 11A, the droplet may undergo Ostwald ripening. Ostwald ripening is a thermodynamically-driven process that energetically can favor larger droplets over smaller droplets. The molecules on the surface of a droplet may comprise a higher chemical potential for smaller droplets than for larger droplets, which may drive the fusion of droplets. In one example, as shown in FIG. 11A, at a time $t_1$ a medium 1102 may comprise droplets 1112, 1114, and 1116 of varying sizes. At a later time $t_2$ the medium 1102 may comprise droplets 1122 and 1124. As shown, the average size of the droplet population at time $t_2$ may be larger than at time $t_1$. A method of processing a droplet may further comprise, during or after providing conditions sufficient for transfer, the first droplet decreasing in size or the second droplet increasing in size. The first droplet may increase or decrease in size via Ostwald ripening.

In a second example shown in FIG. 11B, the reagents may be transferred between droplets via osmotically driven transport. In this example, the size of an individual droplet may remain substantially the same; however, the concentration of reagent within an individual droplet may change. The wall of the droplet may act as a semipermeable membrane. The wall of the droplet may, for example, comprise a surfactant as described elsewhere herein. As shown in FIG. 11B, at a time $t_1$ a medium 1102 may comprise droplets 1112 and 1114 which may comprise differing concentrations of a reagent 1104. In the illustrated example, droplets 1112 comprise a greater concentration of reagent 1104 than droplets 1114. The chemical potential of droplets 1112 may be greater than droplets 1114 due to the higher concentration of the reagent. The reagent may be transferred via diffusion. In some cases, in order to reduce the gradient in the chemical potential, it may be thermodynamically favorable for reagent molecules to diffuse through medium 1102 from droplets 1112 to droplets 1114. In another example, it may be thermodynamically favorable for a fluid inside of droplets 1114 to diffuse to droplets 1112 through the medium. At a later time $t_2$ the medium 1102 may comprise droplets 1122. As shown, the average concentration of the reagent in the droplet population at time $t_2$ may be closer to equilibrium than at time $t_1$.

In cases where the reagent is insufficiently soluble in the medium 1102, the reagent may diffuse from one droplet to another droplet with the aid of a mediator such as a micelle. In cases where the reagent is sufficiently soluble in the medium, the reagent may diffuse through the medium without a mediator.

Figure 12A:
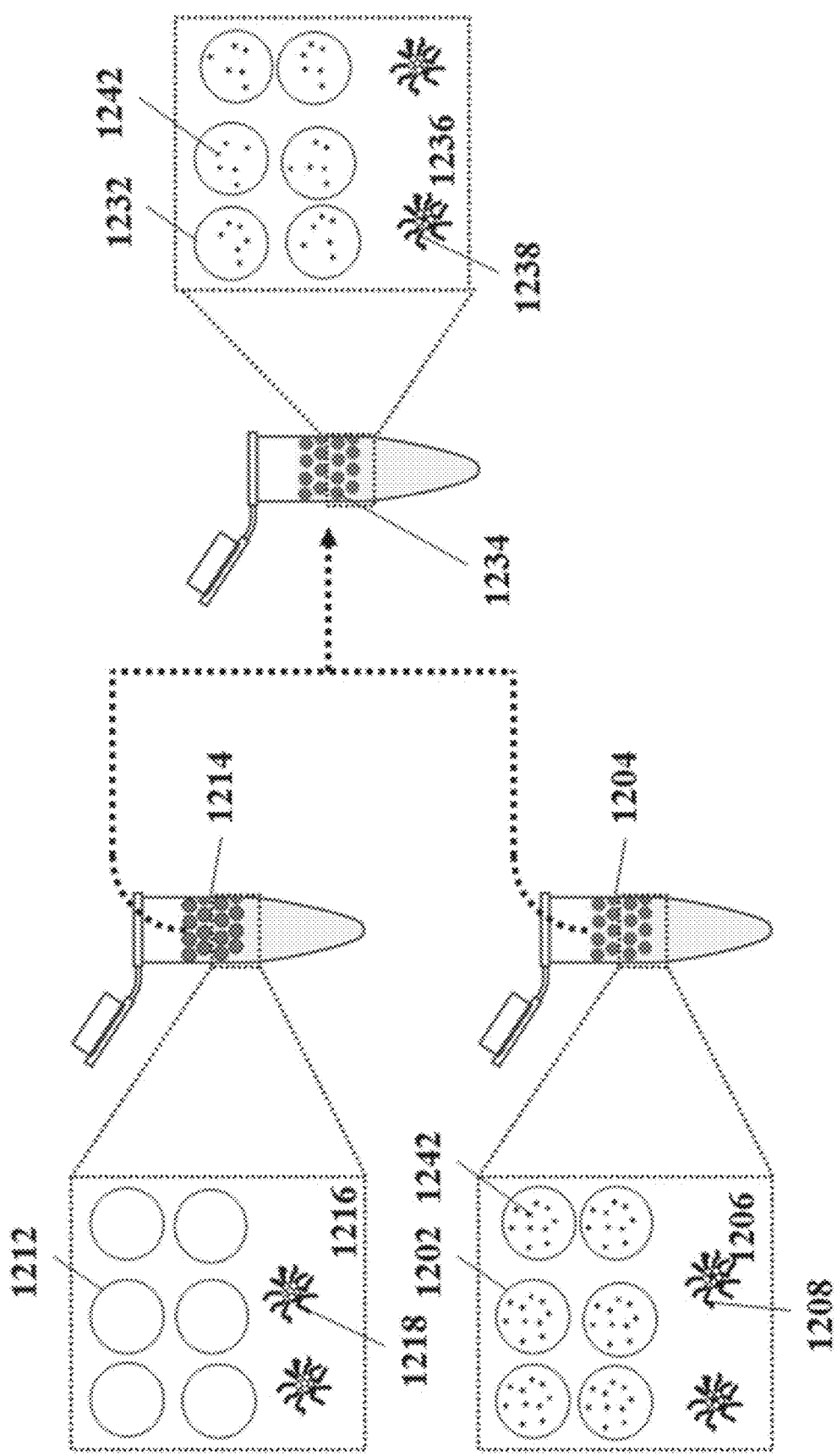
FIG. 12A and FIG. 12B show example methods of processing a droplet.
Figure 12B:
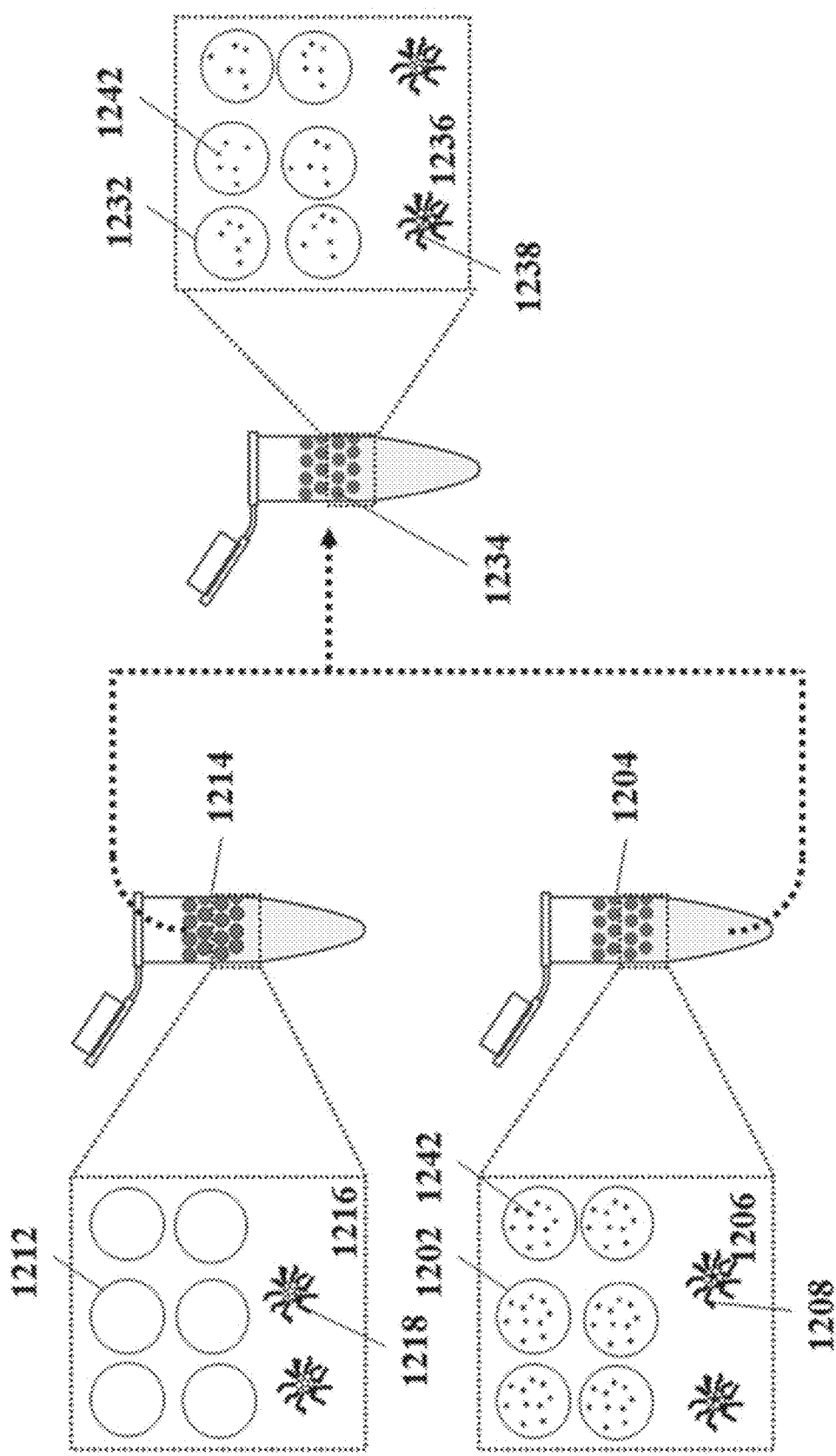

FIG. 12A and FIG. 12B show example methods of processing a droplet. In both methods, a first droplet and a second droplet may be provided. The first droplet 1202 and the second droplet 1212 may comprise droplets in a first population of droplets 1204 and a second population of droplets 1214, respectively. As shown, a first population of droplets 1204 and a second population of droplets 1214 may be provided. The first droplet population may comprise a first droplet fraction and a first fluid fraction 1206, and the second droplet population may comprise a second droplet fraction and a second fluid fraction 1216. The first droplet population may comprise the reagent at a first concentration. The first droplet fraction may comprise droplets which comprise the reagent at a first concentration as described herein. In some cases, the first fluid fraction comprises micelles 1208 which may comprise the reagent. The second droplet population may not comprise the reagent. In some cases, the second droplet population may comprise the reagent at a concentration less than the first droplet population. In some cases, the second droplet fraction may not comprise the reagent. In some cases, the second droplet fraction comprises droplets comprising a reagent at a second concentration less than the concentration of the first droplet fraction. The second droplet fraction may comprise droplets comprising the reagent at a second concentration as described herein. In some cases, the second fluid fraction comprises micelles 1218 which may not comprise the reagent. In another case, the second fluid fraction comprises micelles which comprise the reagent and which can be at a concentration less than the first fluid fraction.

In some cases, the first droplet population and the second droplet population are provided in a first container and a second container respectively. In another case, the first droplet population and the second droplet population may be provided via streams or channels in a microfluidic device as described elsewhere herein. The first and the second droplet populations may be provided via a variety of different fluid sources or receiving components, including reservoirs, tubing, manifolds, or fluidic components of other systems as described elsewhere herein.

FIG. 12A shows an example of a method for processing a droplet. As shown, a first population of droplets 1204 and a second population of droplets 1214 may be provided. The first and the second population may comprise different concentrations of reagents as described herein. Subsequently, the droplets 1202 from the first population may be added to droplets 1212 from the second population to form a mixture 1234. The mixture may comprise a fluid fraction 1236, which may contain micelles 1238. The mixture may comprise droplets 1232 (e.g., droplets to which reagent is/was transferred). The reagent 1242 may be transferred from the second population to the first population, such as via a mediator. The reagent may be transferred from the first droplet to the second droplet within the mixture via diffusion, such as diffusion of the reagents from the first droplet to the second droplet. Such diffusion may be facilitated by the micelle 1208. In some cases, alternatively or in addition to diffusion, other forms of mass transfer or transport phenomena such as convection, heat-mediated mass transfer, turbulent mass transfer (e.g., caused by mixing, agitation, vortexing, shear stress, and/or fluid flow), and/or other forms of mass transfer may also be involved.

In some cases, a method of processing a droplet may additionally comprise, generating a mixture comprising the first droplet and the second droplet, after providing a first droplet and a second droplet. The reagent may be transferred from the first droplet to the second droplet within the mixture. The reagent may be transferred from the first droplet to the second droplet by any mode described herein.

FIG. 12B shows another example method for processing a droplet. In the illustrated example, the fluid fraction 1206 from the first droplet population may be combined with droplets from the second population 1212 to form a mixture 1234. The mixture may comprise a fluid fraction 1236, which may contain micelles 1238. The mixture may comprise droplets 1232 (e.g., droplets to which reagent is/was transferred). In another example, the fluid fraction from the second droplet population 1214 may be combined with droplets from the first population 1204 to form a mixture 1234. The fluid from the fluid fraction may comprise the reagent, and the reagent may be transferred from the fluid fraction to the droplet population. In some cases, a method of processing a droplet may additionally comprise providing the first droplet in a first container comprising a fluid and providing the second droplet in a second container. The method may further comprise transferring the fluid from the first container to the second container. The fluid fraction 1206 can include micelles 1208 that transfer a reagent from the first droplet population 1202, which then transfer the reagent to the second population of droplets 1212.

Figure 13:
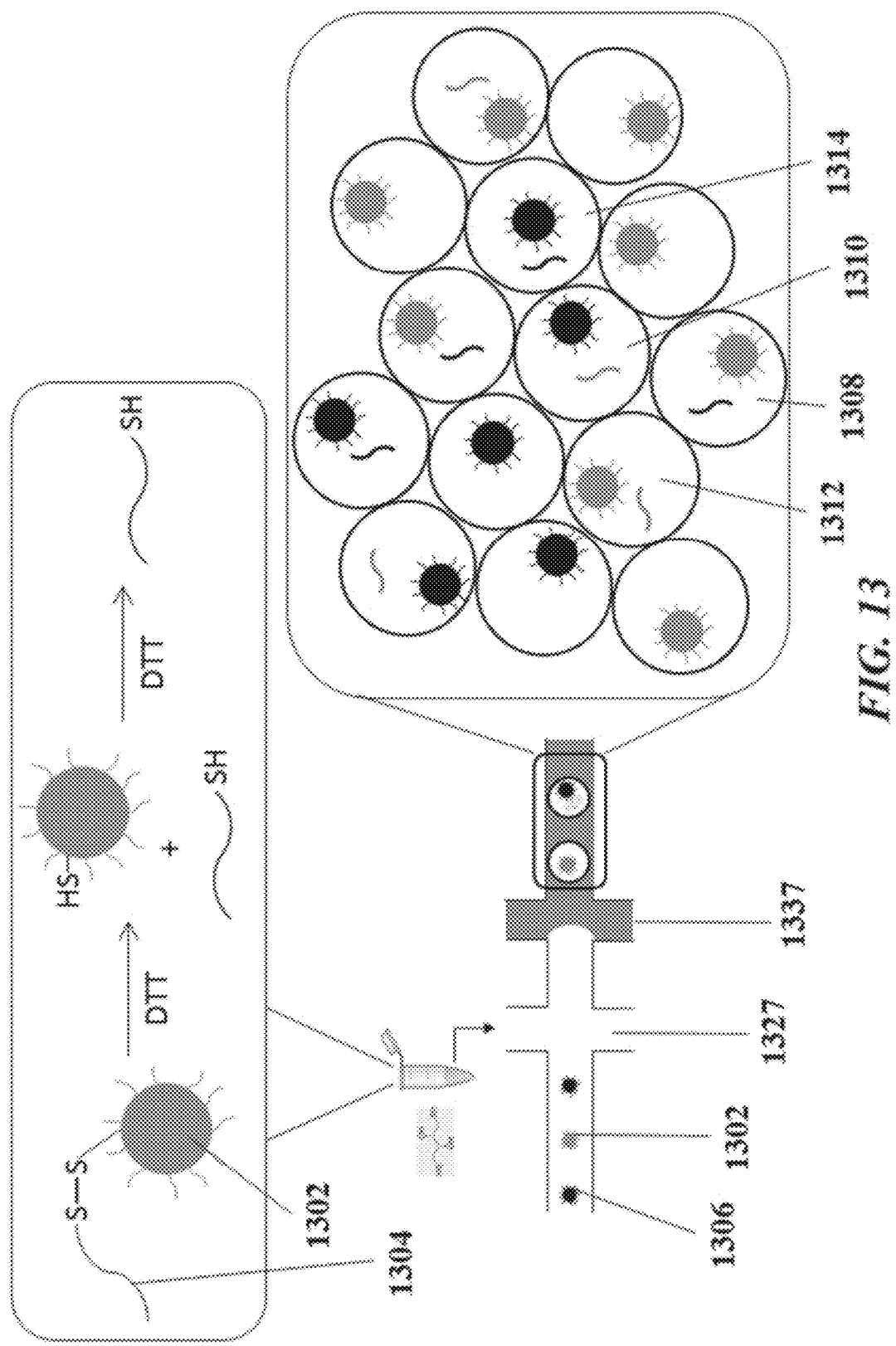
FIG. 13 shows an example method of processing a droplet.

FIG. 13 shows an example method of processing a droplet using a gel bead and a reducing agent. In the inset of FIG. 13, a reaction showing the interaction of DTT with a bead 1302 is shown. As shown, the bead 1302 may comprise molecules 1304 bound to the surface of the bead via a disulfide bond. The molecules may be nucleic acid molecules bound to the surface of the bead. The bead may comprise nucleic acid barcode molecules bound to the surface of the bead. The reagent may be a reducing agent, and the bead may comprise a disulfide that is broken by the reducing agent. In some examples, the reagent may also dissolve the bead (e.g., breaking disulfide bonds of the bead as described elsewhere herein) and/or may release at least a portion of the nucleic acid molecules from the bead. In some cases, the reagent may dissolve a gel bead. For example, the reducing agent may be dithiothreitol (DTT), a functional derivative thereof or any other suitable reducing agent including those described elsewhere herein.

FIG. 13 also shows an example microfluidic device showing a plurality of beads in an aqueous phase of a channel. In some cases, the beads may be provided via a variety of different fluid sources or receiving components, including reservoirs, tubing, manifolds, or fluidic components of other systems. As shown, the beads may comprise different molecules bound to the surface of the bead. For example, a first bead 1302 may comprise a molecule of a first type (e.g., a first nucleic acid barcode molecule having a first barcode sequence) and a second bead 1306 may comprise a molecule of a second type (e.g., a second nucleic acid barcode molecule having a second barcode sequence). From a first channel 1327 of the device, a reagent, such as a reducing agent (for example, DTT, TCEP, etc.), may be added to the beads, forming an aqueous mixture. As the reagent is added to the channel 1327, the reagent may begin reacting with the beads. In some examples, the reagent begins reducing the bonds connecting the surface molecules to the beads. At a second channel 1337 of the device, the resulting aqueous mixture is contacted with an immiscible phase, such as an oil (for example a fluorinated oil may be added to the channel), to form droplets. FIG. 13 shows an enlarged illustration of the droplet population in the channel. The enlarged illustration shows droplets with varying compositions. The varying droplet conditions may comprise different reaction products. A droplet 1308 may comprise a bead of a first type and an unbound surface molecule of a second type. A droplet 1310 may comprise a bead of a second type and an unbound surface molecule of a first type. A droplet 1312 may comprise a bead of a first type and an unbound surface molecule of a first type. A droplet 1314 may comprise a bead of a second type and an unbound surface molecule of a second type.

As shown in FIG. 13, droplet processing in this example can result in a plurality of different types of droplets after the addition of reagent, such as DTT. For example, droplets 1308 and 1310 may comprise a bead comprising bound surface molecules which are different than unbound surface molecules with the droplet. In some cases, the droplet resulting from the method of FIG. 13 may result in droplets with a plurality of types of barcode molecules within a single droplet.

Figure 14:
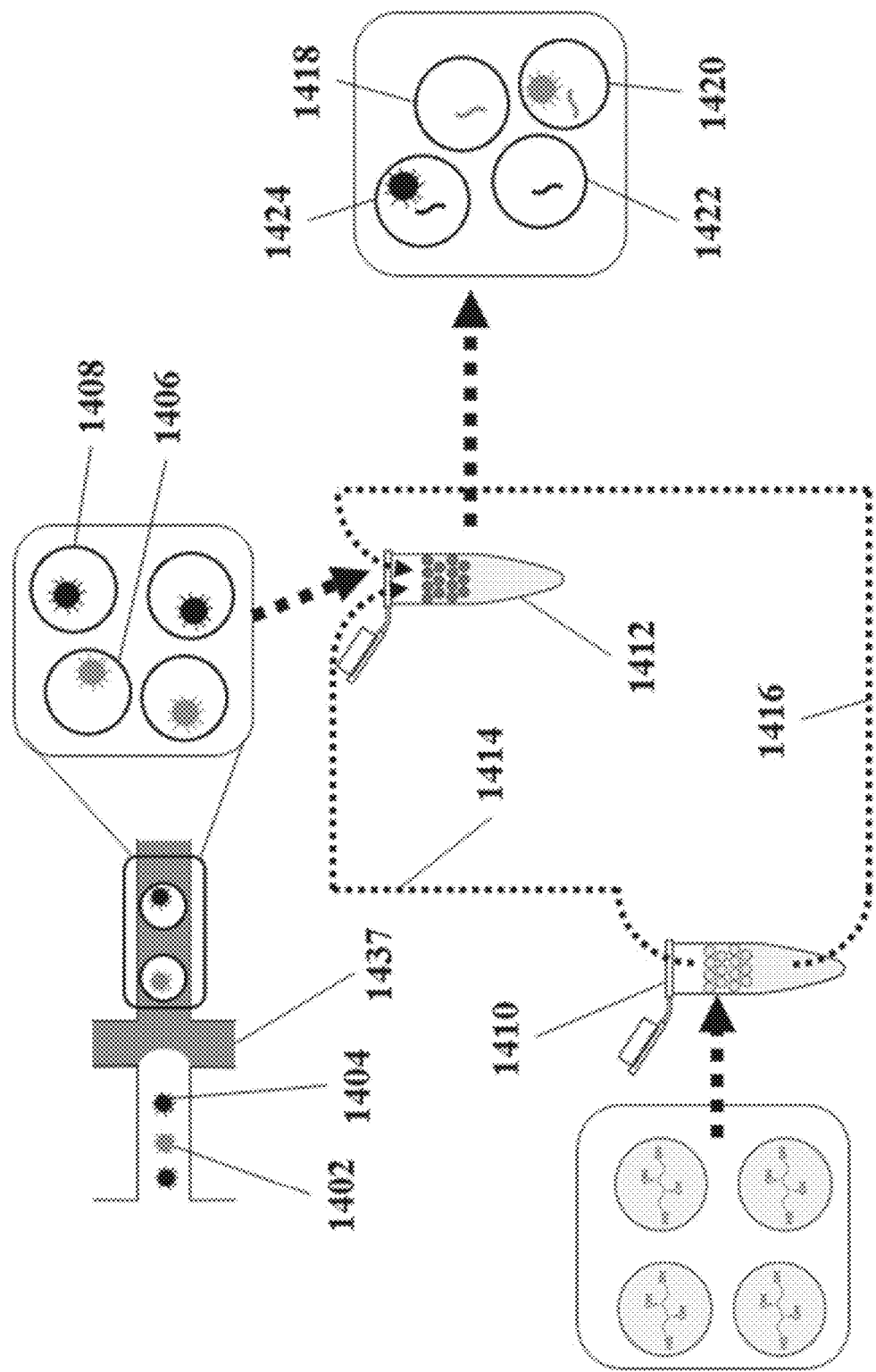
FIG. 14 shows an example method of processing a droplet.

In some cases, methods described herein can be used to generate droplets that include molecules that are derived from a single bead and, thus, are of a single type (e.g., nucleic acid barcode molecules each having the same barcode sequence). Different from the example of FIG. 13, FIG. 14 shows another example implementation of the method of processing a droplet using a bead and a reagent. FIG. 14 shows an example microfluidic device transporting a plurality of beads in an aqueous phase of a channel. In some cases, the beads may be provided via a variety of different fluid sources or receiving components, including reservoirs, tubing, manifolds, or fluidic components of other systems. As shown, the beads may comprise different molecules bound to the surface of the bead. For example, a first bead 1402 may comprise a molecule of a first type (e.g., a first nucleic acid barcode molecule having a first barcode sequence) and a second bead 1404 may comprise a molecule of a second type (e.g., a second nucleic acid barcode molecule having a second barcode sequence). At a channel 1437 of the microfluidic device, the aqueous phase is contacted with an immiscible phase, such as an oil (for example a fluorinated oil may be added to the channel), to form droplets. FIG. 14 shows an enlarged illustration of the droplet population in the channel. The enlarged illustration shows droplets with varying compositions. A droplet 1406 may comprise a bead of a first type. A droplet 1408 may comprise a bead of a second type.

FIG. 14 also shows the methods of FIG. 12A and FIG. 12B in conjunction with the formation of droplets shown at the top of FIG. 14. A first droplet population 1410 may comprise a reagent, such as a reducing agent. In some examples, the reagent is DTT. A second droplet population 1412 may comprise the droplet population of the microfluidic device above. At an arrow 1414, droplets from the first population may be added to droplets of the second population, similar to the example method shown in FIG. 12A. At an arrow 1416, liquid (e.g., a fluid fraction) from the first droplet population may be added to the second droplet population, similar to the example method shown in FIG. 12B. The reagent may transfer to the second droplet via a mode of transferring described herein. As the fluid and/or droplets are added, the reagent may begin reacting with the beads. In some examples, the reagent begins reducing the bonds connecting the surface molecules to the beads. FIG.

14 shows an enlarged illustration of the droplet population. The enlarged illustration shows droplets with varying compositions. The varying droplet conditions may comprise different reaction products. A droplet 1418 may comprise a bead of a first type and an unbound surface molecule of a first type. A droplet 1420 may comprise a dissolved bead of a first type and an unbound surface molecule of a first type. A droplet 1422 may comprise a bead of a second type and an unbound surface molecule of a second type. A droplet 1424 may comprise a dissolved bead of a second type and an unbound surface molecule of a second type. The resulting droplets may comprise reaction products of a substantially similar type.

As shown in FIG. 14 droplet processing in this example can generate droplets comprising reaction products of a substantially similar type after the addition of a reagent, such as DTT. For example, droplets 1418 and 1422 may comprise a bead comprising bound surface molecules which are of the same type as the unbound surface molecules within the droplet. In some cases, droplet processing in this example may result in droplets comprising surface molecules of the same type within the droplet, such as droplets 1418, 1420, 1422, and 1424. In some cases, droplet processing in this example can generate droplets with a single type of barcode molecule (e.g., barcode molecules having the same barcode sequence) within the droplet.

Methods for droplet processing described herein can be implemented with droplets comprising any suitable species and can also be implemented to initiate reactions of any type. For example, droplets may comprise labelling agents (e.g., antibodies) coupled to nucleic acid barcode molecules, with a barcode sequence that identifies it associated antibody, via labile bonds (e.g., disulfide bonds) as is described in U.S. Patent Publication No. 2015/0376609, U.S. patent application Ser. No. 15/720,085 and PCT Application No. PCT/US2017/068320, each of which documents is herein incorporated by reference for all purposes. Methods described herein can be used to transfer reagents from droplets comprising a reagent that breaks the labile bond, initiating release of the nucleic acid barcode molecules from the labelling agent. For example, reducing agents from a first population of droplets may be transferred to a second population of droplets each comprising labelling agents linked to nucleic acid barcode molecules coupled to the labelling agents. Transfer of the reducing agents to the second population of droplets initiates release of nucleic acid barcode molecules from the labelling agents. Such released nucleic acid barcode molecules can then participate in barcoding reactions as is described elsewhere herein and in U.S. Patent Publication No. 2015/0376609, U.S. patent application Ser. No. 15/720,085 and PCT Application No. PCT/US2017/068320. Accordingly, the second droplet may comprise an antibody coupled to a nucleic acid molecule and, in some cases, the reagent may be capable of breaking a linkage between the antibody and the nucleic acid molecule.

The present disclosure provides a method for droplet processing. The method comprises: (a) providing a first droplet population and a second droplet population, wherein droplets from the first droplet population have a first concentration of a reagent and droplets from the second droplet population have a second concentration of the reagent, and wherein the droplets from the second droplet population comprise a bead or an analyte carrier; and (b) providing the first droplet population and the second droplet population with conditions sufficient to transfer the reagent between the first and the second droplet populations, thereby changing the first concentration in the first droplet population and the second concentration in the second droplet population.

In some examples, the method further comprises, in (a), the reagent is absent from the second droplet. In some examples, the reagent is selected from the group consisting of a reducing agent, sodium ion (Na+), magnesium ion (Mg2+), potassium ion (K+), ammonium ion (NH4+), chloride (Cl—), bromide (Br—), iodide (I—), fluoride (F—), adenosine triphosphate (ATP), dinucleotide triphosphate (dNTP), dimethyl sulfoxide (DMSO), and dimethylformamide (DMF). In some examples, the reducing agent is dithiothreitol or a functional derivative thereof. In some examples, the first droplet population comprises a first droplet fraction and a first fluid fraction and wherein the second droplet population comprises a second droplet fraction and a second fluid fraction. In some examples, the first or the second fluid fraction comprises a mediator for reagent transfer.

In some examples, in (b), the reagent is transferred from the first droplet population to the second droplet population via the mediator. In some examples, the mediator is derived from the first droplet population. In some examples, the mediator comprises a surfactant. In some examples, the mediator is a micelle. In some examples, (b) comprises providing the first droplet population with conditions sufficient to transfer the reagent from the first droplet fraction to the first fluid fraction, and providing the second droplet population with conditions sufficient to transfer the reagent from the first fluid fraction to droplets from the second droplet population. In some examples, the first fluid fraction is a continuous phase in which the first droplet population is dispersed. In some examples, the continuous phase comprises an oil. In some examples, the first droplet population is provided in a first container comprising the first fluid fraction and the second droplet population is provided in a second container, and wherein (b) further comprises transferring the first fluid fraction from the first container to the second container.

In some examples, the method further comprises, subsequent to (a), generating a mixture comprising the first droplet population and the second droplet population, wherein the reagent is transferred from the first droplet population to the second droplet population within the mixture. In some examples, the reagent is transferred from the first droplet population to the second droplet population within the mixture via diffusion. In some examples, the bead has nucleic acid molecules coupled thereto. In some examples, the nucleic acid molecules are nucleic acid barcode molecules. In some examples, the reagent dissolves the bead or releases at least a portion of the nucleic acid molecules from the bead. In some examples, the bead is a gel bead. In some examples, the reagent dissolves the gel bead. In some examples, the reagent is a reducing agent and the bead comprises a disulfide bond that is broken by the reducing agent. In some examples, the analyte carrier is a cell. In some examples, the analyte carrier is a cell bead. In some examples, the droplets from the second droplet comprise the bead and the analyte carrier.

In some examples, in (a), the first concentration is greater than the second concentration. In some examples, the droplets from the second droplet population comprise an antibody coupled to a nucleic acid molecule. In some examples, the reagent is capable of breaking a linkage between the antibody and the nucleic acid molecule. In some examples, during or subsequent to (b), the droplets from the first droplet population decrease in size or the droplets from second droplet population increase in size. In some examples, prior to (a), the droplets from the first droplet population or the droplets from the second droplet population are generated using a microfluidic device. In some examples, prior to (a), the first droplet population or the second droplet population is generated upon agitation of a mixture of immiscible phases.

Provided herein are methods for formation of a droplet population comprising a bead. For example, a droplet population may comprise droplets each comprising a single bead. The bead may be any bead described herein, such as a gel bead. In some cases, the gel bead may be a gel droplet in a continuous phase, such as an oil. The bead may be a bead from a population of beads. The population of beads may be monodisperse. For example, the population of beads may have substantially uniform size and/or shape. In some instances, the bead may be substantially spherical. In other instances, the bead may comprise other shapes and forms. In some cases, the beads may be generated using a microfluidic device or other methods described herein. Alternatively, beads may be generated without using a microfluidic device. The method may comprise, prior to providing a first droplet population and a second droplet population, wherein the first droplet population comprises a first concentration of a reagent and the second droplet population comprises a second concentration of the reagent different from the first concentration of the reagent, as described elsewhere herein, generating the second droplet population from (i) a first fluid volume comprising a population of beads and a population of analyte carriers and (ii) a second fluid volume immiscible with the first fluid volume. In some cases, the second droplet population may be generated by applying energy to the first fluid volume, the second fluid volume, and/or both the first and the second fluid volumes. Energy may be mechanical energy. Energy may be provided in the form of agitation, such as vortexing. Energy may be applied in the form of rotation force, mixing, agitation, pulse of energy, shock, stress, shear stress, or other forms of force, stress, or energy. Energy may comprise energy from sound, light, fluid flow, heat, chemical energy, or other types of energy. For example, energy may comprise sonication and/or ultrasound.

The method may comprise generating the second droplet population in absence of using a microfluidic device. In some cases, not using a microfluidic device may simplify the method of generating droplets, and therefore may be less expensive. Generating droplets in absence of using a microfluidic device may be performed with simplified lab equipment and hardware, as well as less specialized operator skills. The method may be capable of being translated and implemented in simple laboratories.

A droplet from the second droplet population may comprise the bead from the population of beads and the analyte carrier from the population of analyte carriers. A droplet from the second droplet population may comprise a single bead from the population of beads. A droplet from the second droplet population may comprise a single analyte carrier, such as a single cell, from the population of analyte carriers.

In some cases, the method may comprise applying a stimulus, such as a form of energy to the mixture. The stimulus and/or energy applied to the first fluid volume and the second fluid volume may comprise mixing and/or agitation. For example, applying the stimulus and/or energy to a first fluid volume and a second fluid volume may comprise mixing and/or agitating the first fluid and the second fluid in a container. In some cases, the second droplet population may be generated by providing a mixture comprising the first fluid volume and the second fluid volume and agitating the mixture. The container may be a tube, a test tube, a PCR tube, a beaker, a flask, a substrate, a box, or other container of any type, size, or scale. Agitating and/or mixing may comprise various mixing techniques, such as vortexing, tube flicking, pipetting, other mixing techniques, and combinations thereof.

The first fluid volume may comprise an aqueous fluid. The second fluid volume may comprise an oil. The first fluid volume and the second fluid volume may comprise any pair of immiscible fluids.

In some examples, the first fluid volume may not contain the reagent or have minimal or negligible concentrations of the reagent. In some examples, the first fluid volume may have any concentration of the reagent.

In some examples, the droplet may comprise a single bead and a single analyte carrier. In some cases, the analyte carrier may be a cell, a cell bead, or a cell nucleus. In some cases, the analyte carrier may be or comprise any analyte, such as a nucleic acid molecule.

In some cases, the method may comprise adding the first fluid comprising a plurality of beads and a plurality of analyte carriers to a container, such as a tube. In some instances, the container may be a centrifuge tube. In some instances, the first fluid may further comprise a first concentration of a reagent. The first concentration may be relatively low or close to zero. For example, the first fluid may have no, or negligible concentrations of, the reagent. In some cases, an excess amount of liquid (e.g., aqueous phase) in the first fluid may be present in the container. Optionally, any amount of excess liquid is removed from the container prior to adding in the second fluid to the container. The removal of the excess liquid from the container may contribute to optimizing subsequent droplet generation, such as for example, fewer resulting small and/or empty droplets. For example, excess liquid may be removed using a pipette or other device. The second fluid may be added to the container. The second fluid may comprise oil or other fluid that is immiscible with the first fluid. In some cases, the second fluid may comprise a surfactant. In some cases, the first fluid may further comprise a surfactant. The mixture of the first fluid and the second fluid may be mixed and/or agitated, or otherwise stimulated. Agitation may comprise vortexing. Agitation may be uniform or substantially uniform. Agitating the mixture may emulsify the mixture, thereby compartmentalizing the first fluid into droplets in a continuous fluid (e.g., the second fluid).

In some cases, the resulting droplet population may comprise droplets of similar size or substantially similar size. Droplets may be monodisperse or substantially monodisperse. In some cases, droplets may be generated in a variety of sizes and not be monodisperse. Generating monodisperse droplets may be favorable for downstream operations (e.g., single cell assays), such as by improving the likelihood of partitioning single analyte carriers in the droplets. The presence of the population of beads in the first fluid may contribute to generating monodisperse droplets. In some cases, at least a portion of the droplets may each comprise a single bead. Some droplets may be empty. Empty droplets may be smaller than droplets comprising beads, and therefore may contain smaller sample amounts. Other droplets may comprise more than one bead. Beads may act as templates during droplet formation to generate monodisperse droplets. The method may comprise generating droplets without using a microfluidic device. Beads may be rigid, semi-rigid, or substantially rigid. Beads (or particles) may resist droplet breakup below the bead size.

In some cases, droplets may be generated without using beads. In such examples, the first fluid may not comprise beads. A first fluid comprising analyte carriers and, in some cases, further comprising a reagent, may be added to a container. The second fluid may be further added to the container. The mixture may be mixed and/or agitated for example by vortexing. The first fluid may be compartmentalized as a dispersed phase in the continuous second fluid. In some cases, droplet populations generated using a first fluid volume comprising the beads may be more monodisperse than droplet populations generated using fluid volumes without the beads described herein.

Mixing speed, such as vortex speed, and mixing duration may be determined and adjusted as necessary. For example, a mixing duration of at least about 30 seconds(s), 40 s, 50 s, 60 s, 70 s, 80 s, 90 s, 100 s, or more may be used. Alternatively or in addition, the mixing duration may be at most about 100 s, 90 s, 80 s, 70 s, 60 s, 50 s, 40 s, 30 s, or less. For example, a vortex speed of at least about 2000 revolutions per minute (rpm), 2100 rpm, 2200 rpm, 2300 rpm, 2400 rpm, 2500 rpm, 2600 rpm, 2700 rpm, or other vortex speeds may be used. In some cases, a vortex speed may be at most about 2000 revolutions per minute (rpm), 2100 rpm, 2200 rpm, 2300 rpm, 2400 rpm, 2500 rpm, 2600 rpm, 2700 rpm, or less. For example, the mixture may be vortexed at 2300 rpm for 30 s. The time to reach the final droplet size and the monodispersity of the emulsion may depend on fluid and/or bead properties. For example, the self-affinity and size of the beads may affect the droplet generation results. Fluid density, viscosity and interfacial tension may affect droplet generation. In some cases, the mixing duration may be independent of total mixture volume. This may be beneficial to the scalability of the process.

Beads may be introduced into the droplets by different approaches, such as the methods described elsewhere herein. In some examples, the method may further comprise generating the population of beads. The method may comprise applying a stimulus to a third fluid volume and a fourth fluid volume to generate the population of beads. The population of beads may comprise droplets in an emulsion (e.g., gel droplets in a continuous phase). In some examples, a population of beads may be generated using similar methods for generating droplets as described herein. For example, the population of beads may be generated with the aid of a microfluidic device and/or by applying a stimulus, such as agitation, such as vortexing, to generate the beads. The population of beads may be further encapsulated in droplets using any of the methods described herein (e.g., by applying stimulus and/or energy, using a microfluidic device, etc.).

In some examples, the method may further comprise generating the population of analyte carriers. In some cases, the population of analyte carriers may comprise a plurality of transposed nuclei. The method may further comprise subjecting a population of cell nuclei to transposition in bulk to yield the plurality of transposed nuclei. The method may further comprise mixing the plurality of transposed nuclei and beads to provide the first fluid. In some instances, the beads (e.g., gel beads) may comprise one or more nucleic acid barcode molecules coupled thereto. The first fluid may comprise transposed nuclei. The first fluid may further comprise one or more biochemical reagents. The first fluid may further comprise beads. The first fluid comprising the transposed nuclei, biochemical reagent(s), and beads may be added to a container such as a tube. In some cases, excess liquid in the first fluid may be removed from the container. The mixture may be agitated by, for example, vortexing. Agitation may emulsify the mixture to generate droplets. Generated droplets may comprise transposed nuclei. Generated droplets may further comprise beads, such as barcoded beads comprising one or more nucleic acid barcode molecules coupled thereto as described elsewhere herein. Some generated droplets may comprise transposed nuclei and beads. Some generated droplets may each comprise a single transposed nucleus and a single bead.

The method may further comprise, subsequent to subjecting the first droplet population and the second droplet population to conditions sufficient to transfer the reagent between the first droplet population and the second droplet population, using a nucleic acid molecule derived from the analyte carrier and a nucleic acid barcode molecule coupled to the bead to generate a barcoded nucleic acid molecule. For example, the first fluid may comprise transposed nuclei, one or more biochemical reagents, and a plurality of barcoded beads. Agitation may emulsify the mixture to generate droplets. At least a subset of the generated droplets may comprise transposed nuclei and barcoded beads.

The method may further comprise subjecting the first droplet population and the second droplet population to conditions sufficient to transfer the reagent between the first droplet population and the second droplet population. In some cases, the reagent may be a reducing agent. In some examples, the reagent may be dithiothreitol (DTT). The reagent may be transported between the first droplet population and the second droplet population using the methods described elsewhere herein, such as with the aid of a mediator, such as micelle. The transfer of DTT to the droplet may dissolve the beads. The transfer of a reducing agent (e.g., DTT) to the droplet may dissolve the beads and/or facilitate release of nucleic acid molecules coupled thereto in the droplets. In some cases, the reagent may comprise a lysis agent. The transfer of a lysis agent to the droplet may facilitate lysis of the analyte carrier and/or release of a nucleic acid molecule (or derivative thereof) from the analyte carrier. Droplets may comprise barcoded analyte carriers. Droplet contents may be subjected to amplification, such as for example, linear amplification. The method may further comprise removing the oil from the container. The method may further comprise sequencing the barcoded nucleic acid molecule, or derivative thereof.

The disclosure provides a method for nucleic acid processing, comprising: (a) agitating (i) a first fluid volume comprising a population of beads and a population of analyte carriers and (ii) a second fluid volume immiscible with the first fluid volume, to generate a plurality of droplets. The population of beads may comprise a plurality of nucleic acid barcode molecules. The population of analyte carriers may comprise a plurality of nucleic acid molecules. A first droplet from the plurality of droplets may comprise a bead from the population of beads and an analyte carrier from the population of analyte carriers. The bead may comprise a nucleic acid barcode molecule of the plurality of nucleic acid barcode molecules, and the analyte carrier may comprise a nucleic acid molecule of the plurality of nucleic acid molecules. The first droplet may have a first concentration of a reagent. The reagent may be configured to release the nucleic acid barcode molecule or release the nucleic acid molecule in the droplet. The method may further comprise (b) subjecting the first droplet and a second droplet having a second concentration of the reagent to conditions sufficient to transfer the reagent between the first droplet and the second droplet, thereby changing the first concentration of the reagent in the first droplet and the second concentration of the reagent in the second droplet; and (c) generating a barcoded nucleic acid molecule using the nucleic acid barcode molecule and the nucleic acid molecule in the first droplet.

In some examples, the agitating comprises mixing and/or agitating using techniques such as vortexing, tube flicking, pipetting, or other techniques.

The first fluid volume may comprise an aqueous fluid and the second fluid volume may comprise an oil.

In some examples, the first fluid volume may not include the reagent. In some cases, the first droplet comprises a single bead and a single analyte carrier. The analyte carrier may be a cell. The reagent may be a lysis reagent. The reagent may lyse the cell. The analyte carrier may be a cell bead. The analyte carrier may be a cell nucleus.

The population of analyte carriers may comprise a plurality of transposed nuclei. The method may comprise subjecting a population of cell nuclei to transposition in bulk to yield the plurality of transposed nuclei. The method may further comprise sequencing the barcoded nucleic acid molecule, or a derivative thereof.

In some example, the reagent may comprise a reducing agent, lysis agent, sodium ion (Na+), magnesium ion (Mg2+), potassium ion (K+), ammonium ion (NH4+), chloride (Cl—), bromide (Br—), iodide (I—), fluoride (F—), adenosine triphosphate (ATP), dinucleotide triphosphate (dNTP), dimethyl sulfoxide (DMSO), dimethylformamide (DMF), and n-dodecyl-beta-D-maltoside (DBDM). The reducing agent is dithiothreitol or a functional derivative thereof.

The plurality of droplets may be provided in a first droplet fraction and a first fluid fraction. Providing a second droplet having a second concentration of the reagent may comprise providing a second plurality of droplets in a second droplet fraction and a second fluid fraction.

The first fluid fraction or the second fluid fraction may comprise a mediator that may aid in transfer of the reagent between the first droplet and the second droplet.

In some examples the reagent is transferred between the first droplet and the second droplet via the mediator when the first droplet and the second droplet are subjected to conditions sufficient to transfer the reagent between the first droplet and the second droplet, thereby changing the first concentration of the reagent in the first droplet and the second concentration of the reagent in the second droplet. The mediator may comprise a surfactant. In some examples, the mediator is a micelle.

In some examples, the method comprises subjecting the second plurality of droplets to conditions sufficient to transfer the reagent from the second droplet fraction to the second fluid fraction and subjecting the plurality of droplets to conditions sufficient to transfer the reagent from the first fluid fraction to the first droplet fraction. The first fluid fraction may be a continuous phase in which the plurality of droplets may be dispersed. The continuous phase may comprise an oil.

The method may further comprise generating a mixture comprising the plurality of droplets and the second plurality of droplets, wherein the reagent may be between the plurality of droplets and the second plurality of droplets within the mixture.

The reagent may be transferred between the first droplet and the second droplet within the mixture via diffusion. In other examples, other mass transfer mechanisms may be involved. Mass transfer may comprise diffusion. Mass transfer may comprise convection. Mass transfer may be affected by various conditions, such as for example, temperature and fluid properties such as density and viscosity. Heat transfer may further contribute to mass transfer. Temperature may be modulated to alter mass transfer rates. In some cases, samples may be further agitated. Agitating the samples may further increase mass transfer.

In some examples, a bead may comprise a subset of nucleic acid barcode molecules of the plurality of nucleic acid barcode molecules coupled thereto. The reagent may dissolve the bead or in some cases, release a portion of the subset of nucleic acid barcode molecules from the bead.

The bead may be a gel bead. The reagent may dissolve the gel bead. In some examples, the reagent may be a reducing agent and the bead may comprise a disulfide bond that may break by the reducing agent.

In some examples, prior to subjecting the first droplet and the second droplet to conditions sufficient to transfer the reagent between the first droplet and the second droplet, the first concentration may be less than the second concentration.

In some examples, during or subsequent to subjecting the first droplet and the second droplet to conditions sufficient to transfer the reagent between the first droplet and the second droplet, the second droplet may decrease in diameter and/or the first droplet may increase in diameter, and/or both.

Systems and Methods for Sample Compartmentalization

In some examples, the systems and methods described herein provide for the compartmentalization, depositing, or partitioning of one or more particles (e.g., analyte carrier, macromolecular constituents of analyte carrier, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more analyte carrier and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. In some cases, a partition may be unoccupied. For example, a partition may not comprise a bead. A cell bead can be an analyte carrier and/or one or more of its macromolecular constituents encased inside of a gel or polymer matrix, such as via polymerization of a droplet containing the analyte carrier and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Additional mechanisms may also be employed in the partitioning of individual analyte carrier, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one example be accomplished by introducing a flowing stream of particles in an aqueous fluid into a flowing stream or reservoir of a non-aqueous fluid, such that droplets are generated (see generally, e.g., FIGS. 1-7B). Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of analyte carrier per partition, number of beads per partition, etc.). For example, partition occupancy can be controlled by providing the aqueous stream at a certain concentration and/or flow rate of particles. To generate single analyte carrier partitions, the relative flow rates of the immiscible fluids can be selected such that, on average, the partitions may contain less than one analyte carrier per partition in order to ensure that those partitions that are occupied are primarily singly occupied. In some cases, partitions among a plurality of partitions may contain at most one analyte carrier (e.g., bead, DNA, cell or cellular material). In some examples, the various parameters (e.g., fluid properties, particle properties, microfluidic architectures, etc.) may be selected or adjusted such that a majority of partitions are occupied, for example, allowing for a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual analyte carriers. The channel structure 100 can include channel segments 102, 104, 106 and 108 communicating at a channel junction 110. In operation, a first aqueous fluid 112 that includes suspended analyte carriers (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include individual analyte carriers 114 (such as droplets 118). A discrete droplet generated may include more than one individual analyte carrier 114 (not shown in FIG. 1). A discrete droplet may contain no analyte carrier 114 (such as droplet 120). Each discrete partition may maintain separation of its own contents (e.g., individual analyte carrier 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., analyte carrier, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more analyte carriers 114, and (2) unoccupied droplets 120, not containing any analyte carriers 114. Occupied droplets 118 may comprise singly occupied droplets (having one analyte carrier) and multiply occupied droplets (having more than one analyte carrier). As described elsewhere herein, in some cases, the majority of occupied partitions can include no more than one analyte carrier per occupied partition and some of the generated partitions can be unoccupied (of any analyte carrier). In some cases, though, some of the occupied partitions may include more than one analyte carrier. In some cases, the partitioning process may be controlled such that fewer than about 25% of the occupied partitions contain more than one analyte carrier, and in many cases, fewer than about 20% of the occupied partitions have more than one analyte carrier, while in some cases, fewer than about 10% or even fewer than about 5% of the occupied partitions include more than one analyte carrier per partition.

In some cases, it may be useful to minimize the creation of excessive numbers of empty partitions, such as to reduce costs and/or increase efficiency. While this minimization may be achieved by providing a sufficient number of analyte carriers (e.g., analyte carrier 114) at the partitioning junction 110, such as to ensure that at least one analyte carrier is encapsulated in a partition, the Poissonian distribution may expectedly increase the number of partitions that include multiple analyte carriers. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the analyte carriers (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
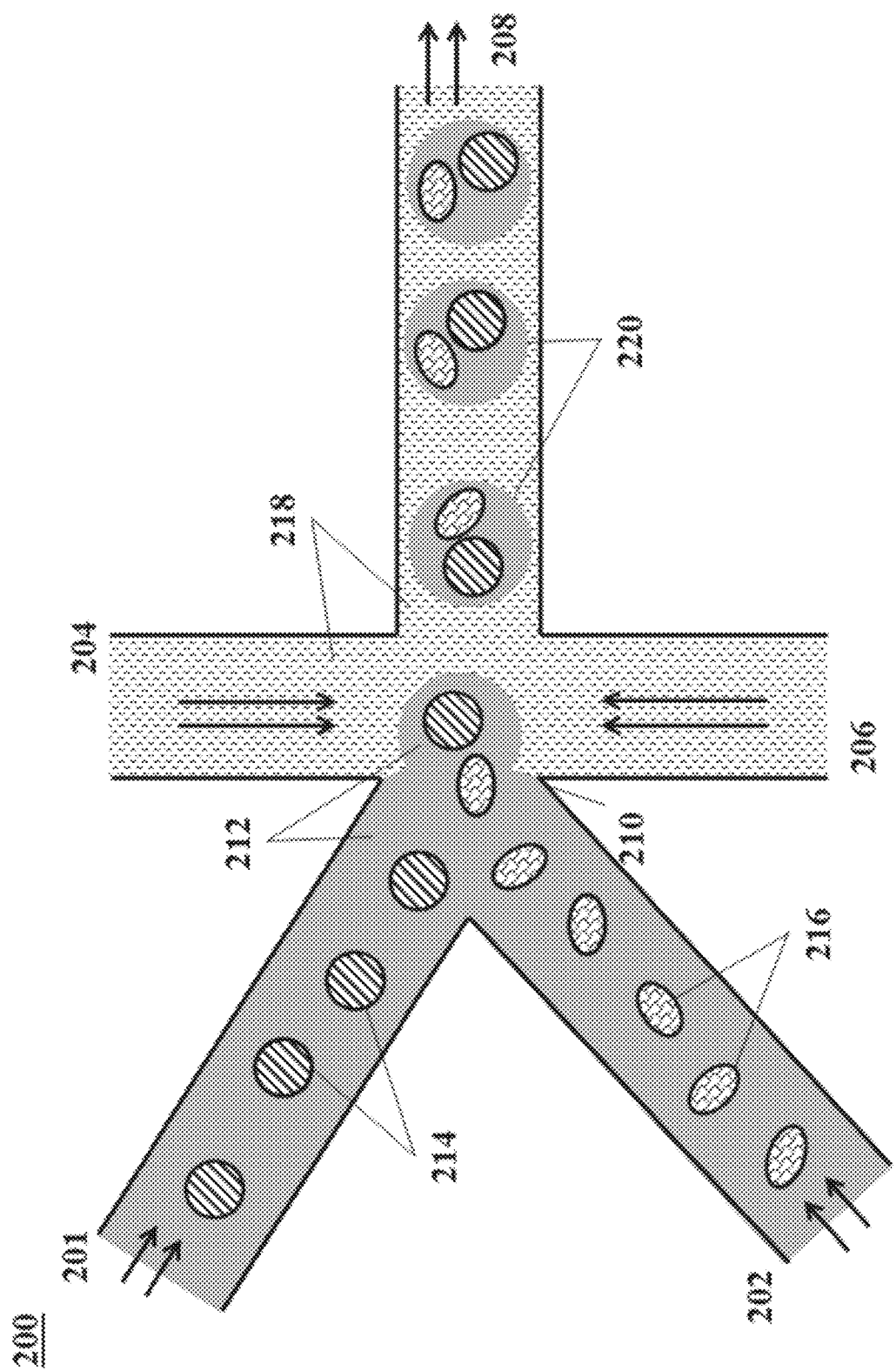
FIG. 2 shows an example of a microfluidic channel structure for delivering barcode carrying beads to droplets.

As will be appreciated, the above-described occupancy rates are also applicable to partitions that include both analyte carriers and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and an analyte carrier.

In another example, in addition to or as an alternative to droplet-based partitioning, analyte carriers may be encapsulated within a microcapsule that comprises an outer shell, layer or porous matrix in which is entrained one or more individual analyte carriers or small groups of analyte carriers. The microcapsule may include other reagents. Encapsulation of analyte carriers may be performed by a variety of processes. Such processes may combine an aqueous fluid containing the analyte carriers with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through crosslinking, polymerization initiation of the precursor (e.g., through added initiators)), mechanical stimuli, or a combination thereof.

Preparation of microcapsules comprising analyte carriers may be performed by a variety of methods. For example, air knife droplet or aerosol generators may be used to dispense droplets of precursor fluids into gelling solutions in order to form microcapsules that include individual analyte carriers or small groups of analyte carriers. Likewise, membrane-based encapsulation systems may be used to generate microcapsules comprising encapsulated analyte carriers as described herein. Microfluidic systems of the present disclosure, such as that shown in FIG. 1, may be readily used in encapsulating cells as described herein. In particular, and with reference to FIG. 1, the aqueous fluid 112 comprising (i) the analyte carriers 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained analyte carriers. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature-based gelling (e.g., upon cooling, etc.).

In some cases, encapsulated analyte carriers can be selectively releasable from the microcapsule, such as through passage of time or upon application of a particular stimulus, that degrades the microcapsule sufficiently to allow the analyte carriers (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The analyte carriers can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the analyte carrier. The polymer or gel may be diffusively permeable to chemical or biochemical reagents. The polymer or gel may be diffusively impermeable to macromolecular constituents of the analyte carrier. In this manner, the polymer or gel may act to allow the analyte carrier to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the analyte carrier may be surrounded by polyacrylamide strands linked together by disulfide bridges. In this manner, the analyte carrier may be encased inside of or comprise a gel or matrix (e.g., polymer matrix) to form a "cell bead." A cell bead can contain analyte carriers (e.g., a cell) or macromolecular constituents (e.g., RNA, DNA, proteins, etc.) of analyte carriers. A cell bead may include a single cell or multiple cells, or a derivative of the single cell or multiple cells. For example, after lysing and washing the cells, inhibitory components from cell lysates can be washed away and the macromolecular constituents can be bound as cell beads. Systems and methods disclosed herein can be applicable to both cell beads (and/or droplets or other partitions) containing analyte carriers and cell beads (and/or droplets or other partitions) containing macromolecular constituents of analyte carriers.

Encapsulated analyte carriers can provide certain potential advantages of being more storable and more portable than droplet-based partitioned analyte carriers. Furthermore, in some cases, analyte carriers can be allowed to incubate for a select period of time before analysis, such as in order to characterize changes in such analyte carriers over time, either in the presence or absence of different stimuli. In such cases, encapsulation may allow for longer incubation than partitioning in emulsion droplets, although in some cases, droplet partitioned analyte carriers may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the analyte carriers into which other reagents are co-partitioned. Alternatively or in addition, encapsulated analyte carriers may be readily deposited into other partitions (e.g., droplets) as described above.

Beads

Nucleic acid barcode molecules may be delivered to a partition (e.g., a droplet or well) via a solid support or carrier (e.g., a bead). In some cases, nucleic acid barcode molecules are initially associated with the solid support and then released from the solid support upon application of a stimulus, which allows the nucleic acid barcode molecules to dissociate or to be released from the solid support. In specific examples, nucleic acid barcode molecules are initially associated with the solid support (e.g., bead) and then released from the solid support upon application of a biological stimulus, a chemical stimulus, a thermal stimulus, an electrical stimulus, a magnetic stimulus, and/or a photo stimulus.

A nucleic acid barcode molecule may contain a barcode sequence and a functional sequence, such as a nucleic acid primer sequence or a template switch oligonucleotide (TSO) sequence.

The solid support may be a bead. A solid support, e.g., a bead, may be porous, non-porous, hollow (e.g., a microcapsule), solid, semi-solid, and/or a combination thereof. Beads may be solid, semi-solid, semi-fluidic, fluidic, and/or a combination thereof. In some instances, a solid support, e.g., a bead, may be dissolvable, disruptable, and/or degradable. In some cases, a solid support, e.g., a bead, may not be degradable. In some cases, the solid support, e.g., a bead, may be a gel bead. A gel bead may be a hydrogel bead. A gel bead may be formed from molecular precursors, such as a polymeric or monomeric species. A semi-solid support, e.g., a bead, may be a liposomal bead. Solid supports, e.g., beads, may comprise metals including iron oxide, gold, and silver. In some cases, the solid support, e.g., the bead, may be a silica bead. In some cases, the solid support, e.g., a bead, can be rigid. In other cases, the solid support, e.g., a bead, may be flexible and/or compressible.

A partition may comprise one or more unique identifiers, such as barcodes. Barcodes may be previously, subsequently or concurrently delivered to the partitions that hold the compartmentalized or partitioned analyte carriers. For example, barcodes may be injected into droplets previous to, subsequent to, or concurrently with droplet generation. The delivery of the barcodes to a particular partition allows for the later attribution of the characteristics of the individual analyte carrier to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of analyte carriers 216 along the channel segment 202 into junction 210. The plurality of biological particles 216 may be sourced from a suspension of analyte carriers. For example, the channel segment 202 may be connected to a reservoir comprising an aqueous suspension of analyte carriers 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and analyte carriers may form a mixture that is directed along another channel to the junction 210 to yield droplets 220. The mixture may provide the beads and analyte carriers in an alternating fashion, such that, for example, a droplet comprises a single bead and a single analyte carrier.

Beads, analyte carriers and droplets may flow along channels at substantially regular flow profiles (e.g., at regular flow rates). Such regular flow profiles may permit a droplet to include a single bead and a single analyte carrier. Such regular flow profiles may permit the droplets to have an occupancy (e.g., droplets having beads and analyte carriers) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual analyte carrier 216. A discrete droplet that is generated may include a barcode or other reagent carrying bead 214. A discrete droplet generated may include both an individual analyte carrier and a barcode carrying bead, such as droplets 220. In some instances, a discrete droplet may include more than one individual analyte carrier or no analyte carrier. In some instances, a discrete droplet may include more than one bead or no bead. A discrete droplet may be unoccupied (e.g., no beads, no analyte carriers).

Beneficially, a discrete droplet partitioning an analyte carrier and a barcode carrying bead may effectively allow the attribution of the barcode to macromolecular constituents of the analyte carrier within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electro-kinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a bead may have a diameter of less than about 10 nm, 100 nm, 500 nm, 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In some cases, beads can be provided as a population or plurality of beads having a relatively monodisperse size distribution. Moreover, relatively consistent amounts of reagents within partitions can be provided while maintaining relatively consistent bead characteristics, such as size, contributing to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in some cases may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide) that comprises one or more functional sequences, such as a TSO sequence or a primer sequence (e.g., a poly T sequence, or a nucleic acid primer sequence complementary to a target nucleic acid sequence and/or for amplifying a target nucleic acid sequence, a random primer, or a primer sequence for messenger RNA) that is useful for incorporation into the bead and/or one or more barcode sequences. The one or more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence (or a portion thereof) for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence (or a portion thereof) for attachment to a sequencing flow cell for Illumina sequencing. In some cases, the nucleic acid molecule can comprise a barcode sequence. In some cases, the nucleic acid molecule can further comprise a unique molecular identifier (UMI). In some cases, the nucleic acid molecule can comprise an R1 primer sequence for Illumina sequencing. In some cases, the nucleic acid molecule can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 8:
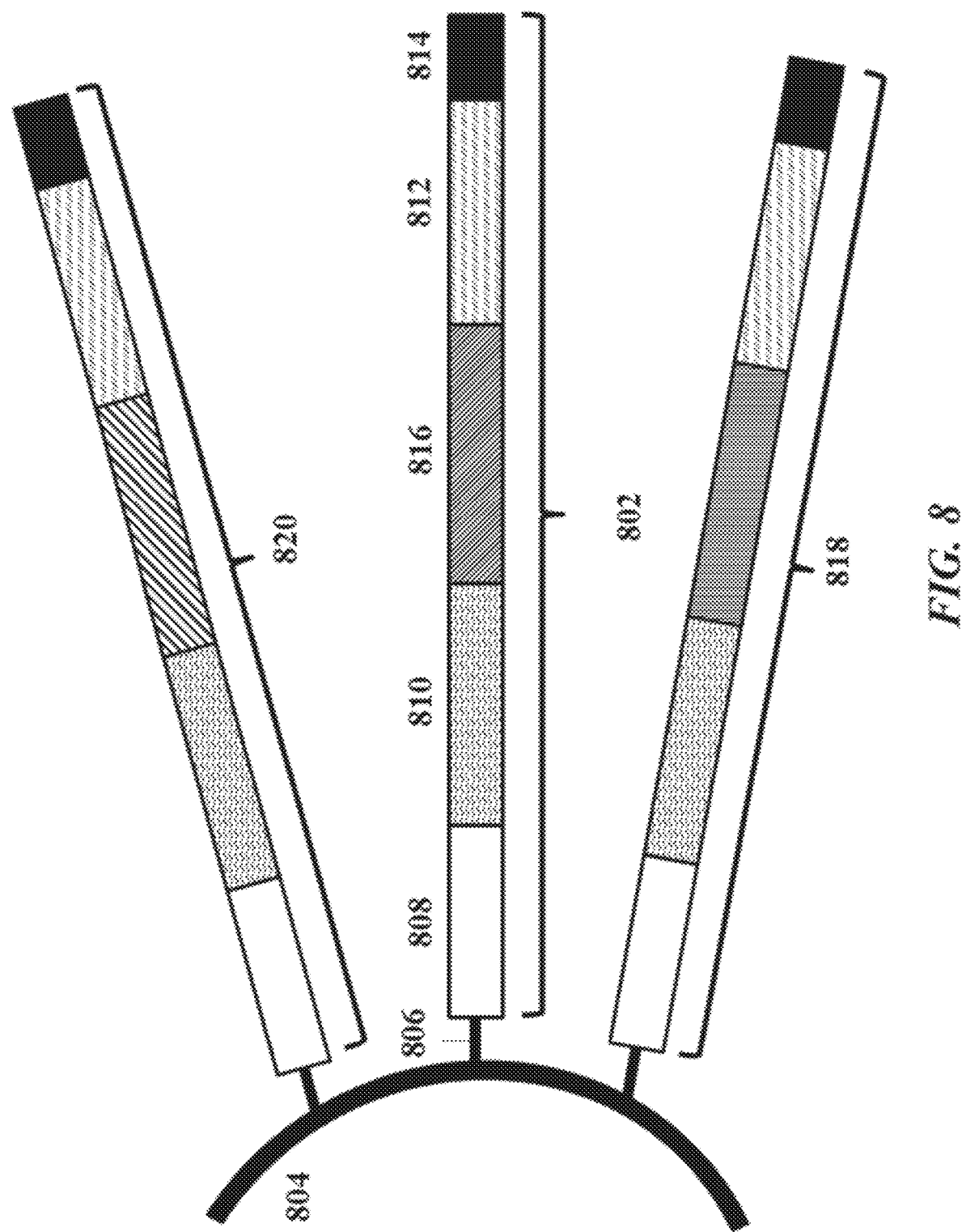
FIG. 8 illustrates an example of a barcode carrying bead.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular identifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 808, 810, 812, etc.) and variable or unique sequence segments (e.g., 816) between different individual nucleic acid molecules coupled to the same bead.

In operation, an analyte carrier (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of a mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the different mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the analyte carrier (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl) cystamine can be co-polymerized together to generate a gel bead comprising free COOH groups. The COOH groups of the gel bead can be activated (e.g., via 1-Ethyl-3-(3-dimethylaminopropyl) carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead.

Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent: gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead can be injected or otherwise introduced into a partition. In some examples, the bead may be generated in a spherical or semi-spherical shape, such as for example, in form of a droplet. A bead can comprise an inner partition in a droplet, such as a droplet core described herein. In some cases, droplet generation methods, such as with the aid of a microfluidic device may be used to generate a plurality of beads. Such generated population of beads may be monodisperse. The plurality of beads may be subjected to conditions sufficient to solidify the beads. Such beads may be further partitioned and/or compartmentalized into droplets using droplet generation techniques. For example, the beads may be compartmentalized in the second droplet population described herein. In some examples, the beads may comprise the inner partition (the core) of the second droplet population. The second droplet population may be generated by applying a stimulus, such as agitation, such as vortexing to compartmentalize the beads into the droplets.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization-based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can break and the bead can get degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead may degrade, and the barcode sequence may be released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it may be useful to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be useful to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but not be limited to pH-mediated changes to the integrity of a component within the bead, degradation of a component of a bead via cleavage of cross-linked bonds, and depolymerization of a component of a bead.

In some examples, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl)phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some examples, changes in temperature or pH may be used to degrade thermo-sensitive or pH-sensitive bonds within beads. In some examples, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some examples, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be useful to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the analyte carrier and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of analyte carriers (e.g., one analyte carrier and one bead per partition).

The partitions described herein may comprise small volumes, for example, less than about 10 microliters (µL), 5 µL, 1 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet-based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned analyte carriers and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In some cases, analyte carriers may be partitioned along with lysis reagents in order to release the contents of the analyte carriers within the partition. In such cases, the lysis agents can be contacted with the analyte carrier suspension concurrently with, or immediately prior to, the introduction of the analyte carriers into the partitioning junction/droplet generation zone (e.g., junction 210), such as through an additional channel or channels upstream of the channel junction. In other examples, additionally or alternatively, analyte carriers may be partitioned along with other reagents, as will be described further below.

Figure 3:
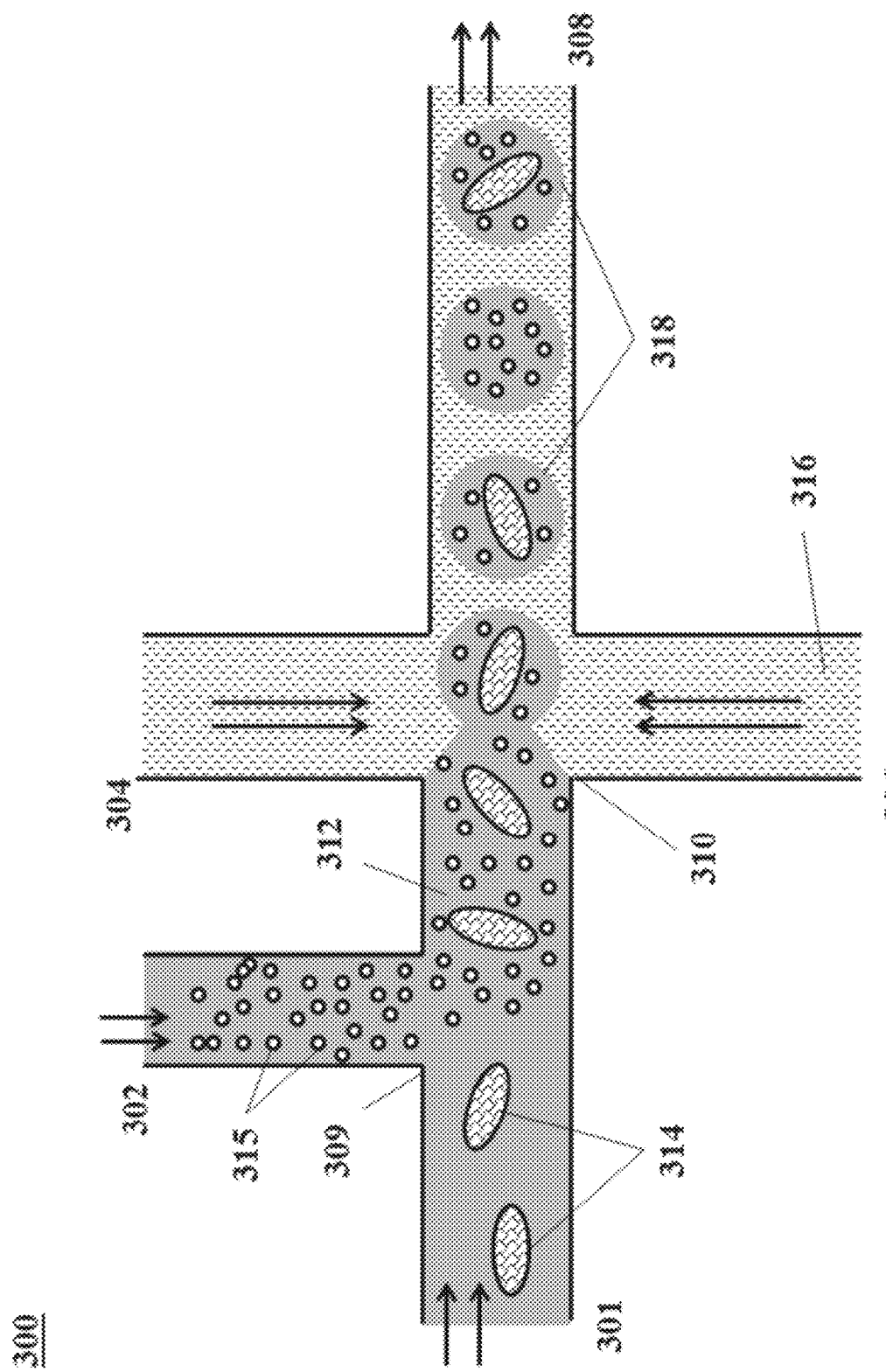
FIG. 3 shows an example of a microfluidic channel structure for co-partitioning analyte carriers and reagents.

FIG. 3 shows an example of a microfluidic channel structure 300 for co-partitioning analyte carriers and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of analyte carriers 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of analyte carriers 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the analyte carriers 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual analyte carrier 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no analyte carriers).

Beneficially, when lysis reagents and analyte carriers are co-partitioned, the lysis reagents can facilitate the release of the contents of the analyte carriers within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or analyte carriers that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Lysis agents may comprise Mammalian Protein Extraction Reagent (MPER). Other lysis agents may additionally or alternatively be co-partitioned with the analyte carriers to cause the release of the analyte carriers' contents into the partitions. For example, in some cases, surfactant-based lysis solutions may be used to lyse cells, although surfactants can interfere with stable emulsions. In some cases, lysis solutions may include non-ionic surfactants such as, for example, Triton® X-100 (t-Octylphenoxypolyethoxyethanol) and Tween® 20 (polysorbate 20). In some cases, lysis solutions may include ionic surfactants such as, for example, Sarcosyl® (sodium lauroyl sarcosinate) and sodium dodecyl sulfate (SDS). Electroporation, thermal, acoustic or mechanical cellular disruption may also be used in certain cases, e.g., non-emulsion-based partitioning such as encapsulation of analyte carriers that may be in addition to or in place of droplet partitioning, where any pore size of the encapsulate is sufficiently small to retain nucleic acid fragments of a given size, following cellular disruption.

Alternatively or in addition to the lysis agents co-partitioned with the analyte carriers described above, other reagents can also be co-partitioned with the analyte carriers, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated analyte carriers (e.g., a cell or a nucleus in a polymer matrix), the analyte carriers may be exposed to an appropriate stimulus to release the analyte carriers or their contents from a co-partitioned microcapsule. For example, in some cases, a chemical stimulus may be co-partitioned along with an encapsulated analyte carrier to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative examples, this may be a different and non-overlapping stimulus, in order to allow an encapsulated analyte carrier to be released into a partition at a different time from the release of nucleic acid molecules into the same partition. For a description of methods, compositions, and systems for encapsulating cells (also referred to as a "cell bead"), see, e.g., U.S. Pat. No. 10,428,326 and U.S. Pat. Pub. 20190100632, which are each incorporated by reference in their entirety.

Additional reagents may also be co-partitioned with the analyte carrier, such as endonucleases to fragment an analyte carrier's DNA, DNA polymerase enzymes and dNTPs used to amplify the analyte carrier's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxy Inosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of analyte carriers, such as RNA, DNA, or proteins) contained therein may be further processed within the partitions. In accordance with the methods and systems described herein, the macromolecular component contents of individual analyte carriers can be provided with unique identifiers such that, upon characterization of those macromolecular components they may be attributed as having been derived from the same analyte carrier or carriers. The ability to attribute characteristics to individual analyte carrier or groups of analyte carriers is provided by the assignment of unique identifiers specifically to an individual analyte carrier or groups of analyte carriers. Unique identifiers, e.g., in the form of nucleic acid barcodes can be assigned or associated with individual analyte carriers or populations of analyte carriers, in order to tag or label the analyte carrier's macromolecular components (and as a result, its characteristics) with the unique identifiers. These unique identifiers can then be used to attribute the analyte carrier's components and characteristics to an individual analyte carrier or group of analyte carriers.

In some cases, this is performed by co-partitioning the individual analyte carrier or groups of analyte carriers with the unique identifiers, such as described above (with reference to FIG. 2). In some cases, the unique identifiers are provided in the form of nucleic acid molecules (e.g., oligonucleotides) that comprise nucleic acid barcode sequences that may be attached to or otherwise associated with the nucleic acid contents of individual analyte carrier, or to other components of the analyte carrier, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some cases, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned analyte carriers. These sequences include, e.g., targeted or random/universal amplification primer sequences for amplifying nucleic acids (e.g., mRNA, genomic DNA) from the individual analyte carriers within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides (e.g., attached to a bead) into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some examples, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, multiple different nucleic acid barcode molecules can be incorporated within a given partition and be either attached to a single bead or to multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) may be releasable from the beads upon the application of a stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of analyte carriers and may be degraded for release of the attached nucleic acid molecules through exposure to a reducing agent, such as DTT.

In some examples, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
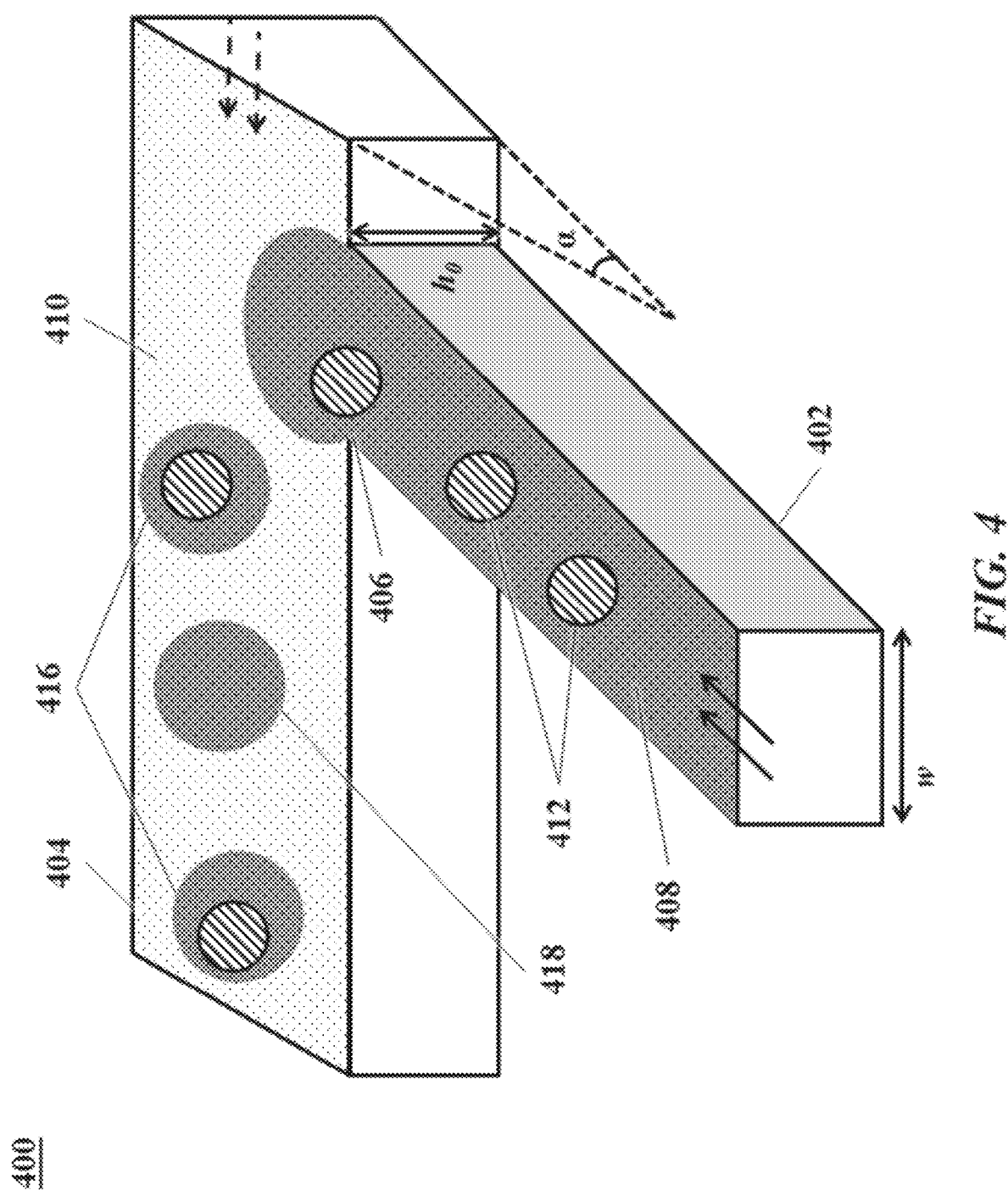
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, α, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more analyte carriers, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise analyte carriers (e.g., described with reference to FIGS. 1 and 2). In some instances, the aqueous fluid 408 can have a substantially uniform concentration or frequency of analyte carriers. As with the beads, the analyte carriers can be introduced into the channel segment 402 from a separate channel. The frequency or concentration of the analyte carriers in the aqueous fluid 408 in the channel segment 402 may be controlled by controlling the frequency in which the analyte carriers are introduced into the channel segment 402 and/or the relative flow rates of the fluids in the channel segment 402 and the separate channel. In some instances, the analyte carriers can be introduced into the channel segment 402 from a plurality of different channels, and the frequency controlled accordingly. In some instances, a first separate channel can introduce beads and a second separate channel can introduce analyte carriers into the channel segment 402. The first separate channel introducing the beads may be upstream or downstream of the second separate channel introducing the analyte carriers.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, $\alpha$. The expansion angle, $\alpha$, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle.

The resulting droplet radius, $R_d$, may be predicted by the following equation for the aforementioned geometric parameters of $h_0$, w, and $\alpha$:

$$R_d \approx 0.44 \left(1 + 2.2\sqrt{\tan\alpha}\, \frac{w}{h_0}\right) \frac{h_0}{\sqrt{\tan\alpha}}$$

By way of example, for a channel structure with w=21 µm, h=21 µm, and $\alpha$=3°, the predicted droplet size is 121 µm. In another example, for a channel structure with w=25 µm, h=25 µm, and $\alpha$=5°, the predicted droplet size is 123 µm. In another example, for a channel structure with w=28 µm, h=28 µm, and $\alpha$=7°, the predicted droplet size is 124 µm.

In some instances, the expansion angle, $\alpha$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (µm) to about 500 µm. In some instances, the width, w, can be between a range of from about 10 µm to about 200 µm. Alternatively, the width can be less than about 10 µm. Alternatively, the width can be greater than about 500 µm. In some instances, the flow rate of the aqueous fluid 408 entering the junction 406 can be between about 0.04 microliters (µL)/minute (min) and about 40 µL/min. In some instances, the flow rate of the aqueous fluid 408 entering the junction 406 can be between about 0.01 microliters (µL)/minute (min) and about 100 µL/min. Alternatively, the flow rate of the aqueous fluid 408 entering the junction 406 can be less than about 0.01 µL/min. Alternatively, the flow rate of the aqueous fluid 408 entering the junction 406 can be greater than about 40 µL/min, such as 45 µL/min, 50 µL/min, 55 µL/min, 60 µL/min, 65 µL/min, 70 µL/min, 75 µL/min, 80 µL/min, 85 L/min, 90 µL/min, 95 µL/min, 100 µL/min, 110 µL/min, 120 µL/min, 130 µL/min, 140 µL/min, 150 µL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
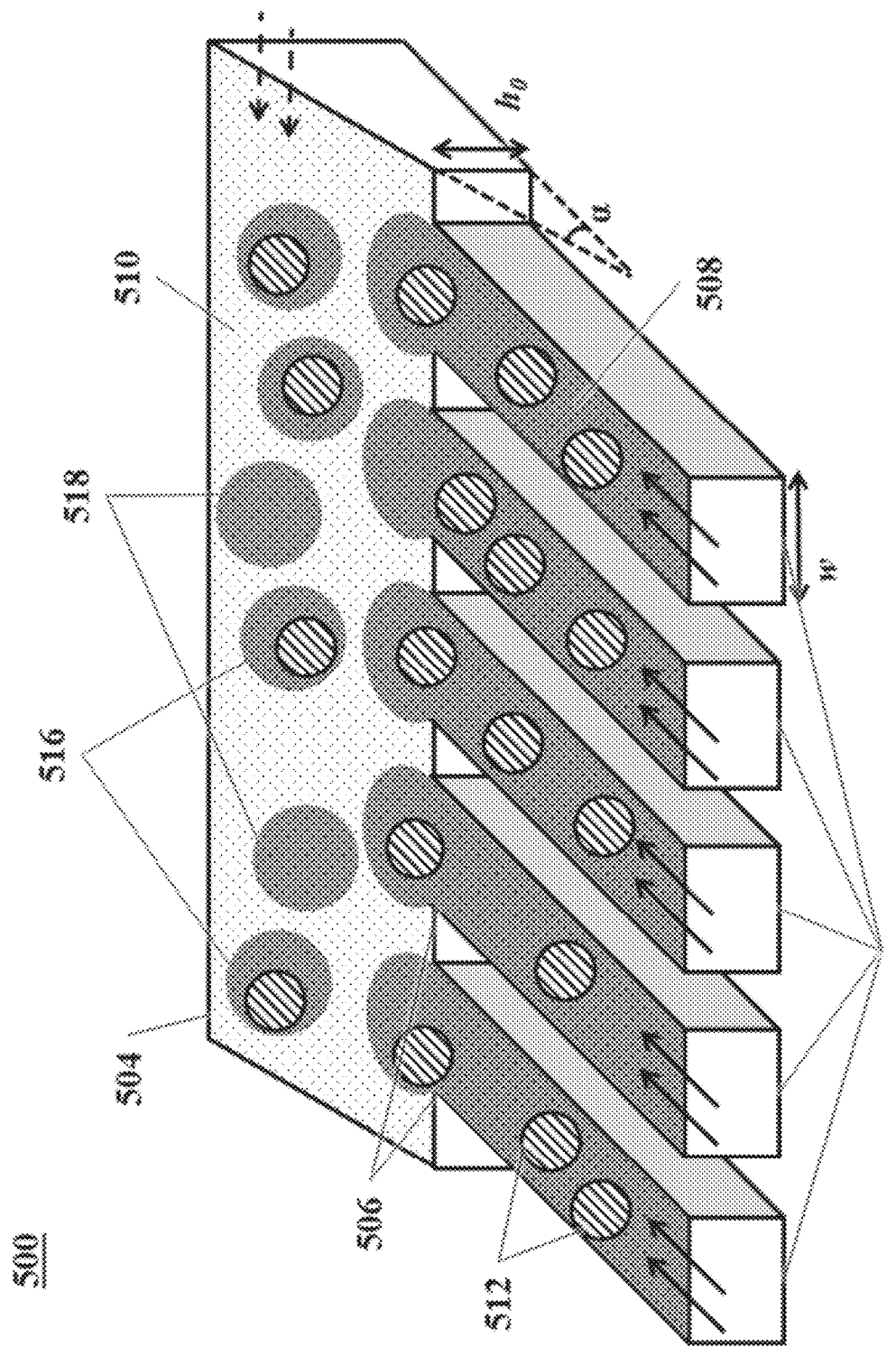
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_0$, α, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and α, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, the geometric parameters for the plurality of channel segments 502 may be varied accordingly to yield different distributions of droplet sizes.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
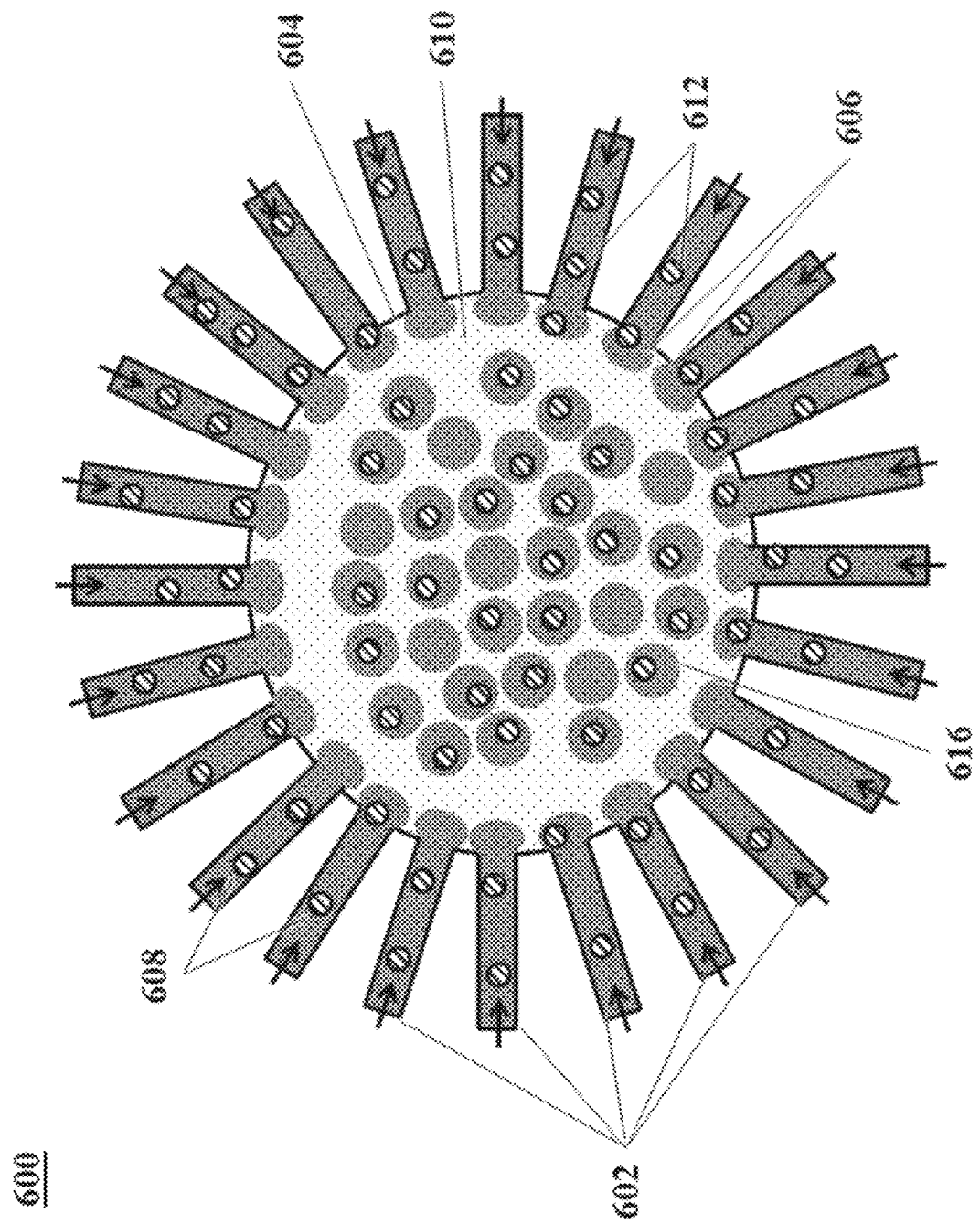
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 2 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, α (not shown in FIG. 6) at or near each channel junction. Each channel segment of the plurality of channel segments 602 may have a width, w, and a height, $h_o$, at or near the channel junction. The geometric parameters, w, $h_o$, and α, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, the geometric parameters for the plurality of channel segments 602 may be varied accordingly to yield different distributions of droplet sizes.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or analyte carrier injected into the droplets may or may not have uniform size.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors such as the hydrodynamic forces at the junction 706, relative flow rates of the two fluids 712, 714, fluid properties, and certain geometric parameters (e.g., $4h$, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, such as a bead, cell bead, gel bead, analyte carrier, macromolecular constituents of analyte carrier, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce analyte carriers into the channel segment 702. The first separate channel introducing the beads may be upstream or downstream of the second separate channel introducing the analyte carriers.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, such as via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of Δh. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, β, at or near the junction 706. The height difference, Δh, and/or expansion angle, β, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, Δh, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 µm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 µm or less. In some instances, the expansion angle, $\beta$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 712 entering the junction 706 can be between about 0.04 microliters (µL)/minute (min) and about 40 µL/min. In some instances, the flow rate of the aqueous fluid 712 entering the junction 706 can be between about 0.01 microliters (µL)/minute (min) and about 100 µL/min. Alternatively, the flow rate of the aqueous fluid 712 entering the junction 706 can be less than about 0.01 µL/min. Alternatively, the flow rate of the aqueous fluid 712 entering the junction 706 can be greater than about 40 µL/min, such as 45 µL/min, 50 µL/min, 55 µL/min, 60 µL/min, 65 µL/min, 70 µL/min, 75 L/min, 80 µL/min, 85 µL/min, 90 µL/min, 95 µL/min, 100 µL/min, 110 µL/min, 120 µL/min, 130 µL/min, 140 L/min, 150 µL/min, or greater. At lower flow rates, such as flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, such as at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, $\Delta h$, being abrupt at the junction 706 (e.g., a step increase), the height difference may increase gradually (e.g., from about 0 µm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, $\beta$), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different analyte carrier or organism types within a population of analyte carriers, including, for example, microbiome analysis and characterization, environmental testing, food safety testing, epidemiological analysis, e.g., in tracing contamination or the like.

Computer Systems

Figure 9:
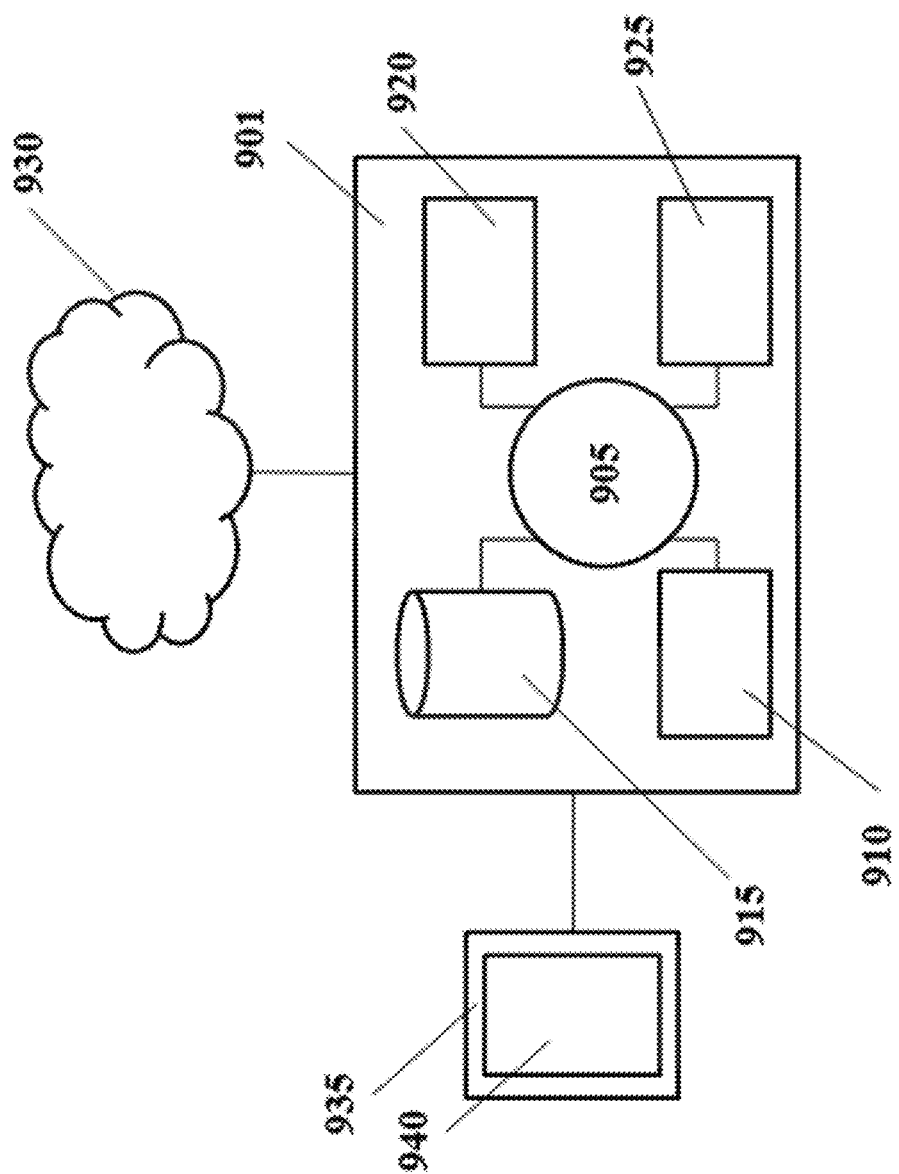
FIG. 9 shows a computer system that is programmed or otherwise configured to implement methods provided herein.

The present disclosure provides computer systems that are programmed to implement methods of the disclosure. FIG. 9 shows a computer system 901 that is programmed or otherwise configured to, for example, process and/or analyze a droplet, control addition of reagent to droplets and/or reaction mixtures, control partition generation, control of reagent addition to partitions, provide conditions sufficient for transfer of a reagent, provide conditions sufficient to conduct reactions, obtain and process sequencing data, output sequencing results to a user, provide an interface for a user to input to control devices coupled to the computer processor. The computer system 901 can regulate various aspects of the present disclosure, such as, for example, regulating fluid flow rate in one or more channels in a microfluidic structure, regulating polymerization application units, etc. The computer system 901 can be an electronic device of a user or a computer system that is remotely located with respect to the electronic device. The electronic device can be a mobile electronic device.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine-readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, monitoring of sample preparation, monitoring droplet preparation, monitoring reagent addition, monitoring of reactions and/or reaction conditions, monitoring sequencing, results of sequencing, and permitting user inputs for sample preparation, reaction, sequencing and//or analysis, etc., Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, implement sample preparation protocols, implement droplet preparation protocols, implement reagent addition protocols, data analysis protocols, perform sequencing protocols, system and/or device operation protocols, etc.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, an analyte carrier (e.g., a cell or cell bead) is partitioned in a partition (e.g., droplet), and multiple analytes from the analyte carrier are processed for subsequent processing. The multiple analytes may be from the single cell. This may enable, for example, simultaneous proteomic, transcriptomic and genomic analysis of the cell.

EXAMPLES

Example 1: Transfer of Reagents Between Droplets

Figure 15B:
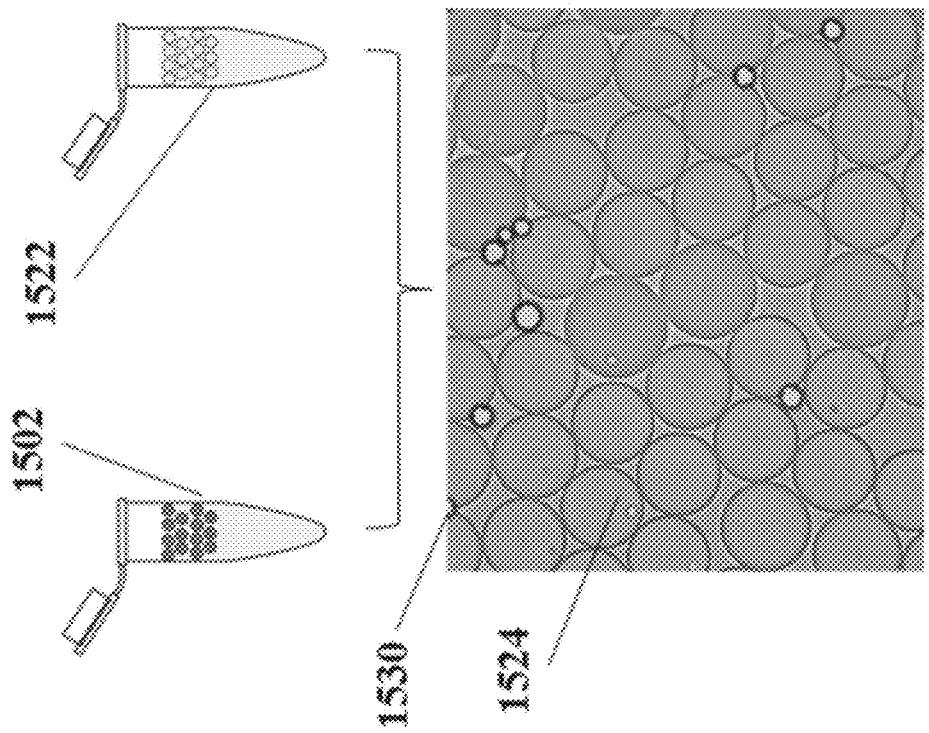
FIG. 15B shows the results of an experiment demonstrating the method of processing a droplet as described in Example 1.
Figure 15A:
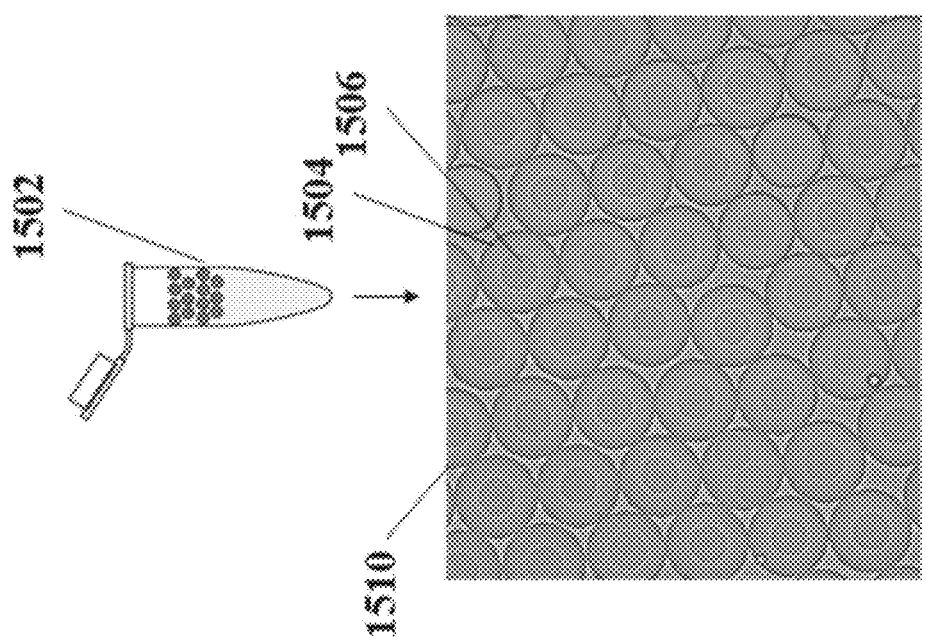
FIG. 15A shows a droplet population comprising gel beads and no DTT.

FIG. 15A shows a droplet population comprising gel beads and no DTT. FIG. 15B shows the results of an experiment demonstrating the method of processing a droplet. FIG. 15A shows a microscope image 1510 of a monodisperse water-in-fluorinated oil emulsion 1502 which was produced using a microfluidic device. In the image 1510, each droplet 1504 may contain a single bead (e.g., a disulfide-bond crosslinked hydrogel bead 1506) and no dithiothreitol (DTT). In some cases, some droplets may contain more than one bead. A droplet, such as droplet 1504 containing a bead 1506 may be referred to herein as a GEM. As shown in 1510, hydrogel beads may be clearly visible inside droplets. A second disperse water-in-fluorinated oil emulsion 1522 was created by shaking to produce droplets which contained a disulfide bond reducing agent (dithiothreitol; DTT). Both droplet populations were then mixed together in the same tube. In FIG. 15B in the image 1530, the result of mixing both populations is shown. As shown, hydrogel beads were no longer visible in each droplet 1524, indicating that DTT had been transported from one droplet population to another and subsequently caused the dissolution of hydrogel beads through reduction of their crosslinking disulfide bonds.

Example 2: Transfer of Reagents Between Droplets

Transport of a reducing agent (e.g., DTT) from one droplet population into another was used to simultaneously measure gene expression and cell surface proteins from single cells as described in U.S. Patent Publication No. 2015/0376609, U.S. patent application Ser. No. 15/720,085 and PCT Application No. PCT/US2017/068320. Cells were labelled with nucleic acid barcode molecule-tagged antibodies that targeted specific cell surface markers. The antibodies were linked to the nucleic acid barcode molecules through a disulfide bond. The labelled cells were then isolated and co-partitioned in aqueous droplets in an oil phase with gel beads comprising nucleic acid barcode molecules. The aqueous droplets were then contacted with a population of droplets containing DTT in a mixture, similar to the example method shown in FIG. 12A. Transfer of DTT from the DTT droplets to those comprising antibody and bead released nucleic acid barcode molecules from beads and antibodies, followed by barcoding of nucleic acid molecules, further processing and sequencing of barcoded constructs as is described elsewhere herein.

Table 1 provides the various conditions used to test for the transfer of reagents between droplets. The mass transport of DTT into droplets each containing a bead (GEMs) after the generation of the GEMs was analyzed for any impact on the ability to the measure gene expression profile of cells. Tables 2A-B provide the results for gene expression measurements/analysis. Tables 3A-B provide the results for cell surface protein measurements/analysis.

TABLE 1

| Sample | Conjugation chemistry | DTT concentration in RT Master Mix | DTT oil or emulsion volume spiked in post-GEM generation |
|---|---|---|---|
| 1 | Non-Disulfide (S-S) | 0.5-500 mM | 0 µl |
| 2 | | 0.5-100 mM | 0 µl |
| 3 | | 0.5-50 mM | 0 µl |
| 4 | | 0.5-20 mM | 0 µl |
| 5 | Disulfide | 0.5-500 mM | 0 µl |
| 6 | (S-S) | 0.5-100 mM | 0 µl |
| 7 | | 0.5-50 mM | 0 µl |
| 8 | | 0.5-20 mM | 0 µl |
| 9 | Non-Disulfide (S-S) | None | 2-10 µl DTT emulsion |
| 10 | | None | 1-10 µl DTT emulsion |
| 11 | Disulfide | None | 1-8 µl oil saturated with DTT |
| 12 | (S-S) | None | 1-5 µl DTT emulsion |
| 13 | | None | 1-5 µl DTT emulsion |
| 14 | | None | ~5 µl GEM oil + 5 µl DTT emulsion |

Table 2A summarizes the cell expression measurements and results for Samples 1-8.

TABLE 2A

| Measurement | Samples 1-4 | Samples 5-8 |
| --- | --- | --- |
| Estimated # of cells | 1059 to 1257 | 1221 to 1305 |
| Mean reads/cell | 40257 to 55865 | 35061 to 60693 |
| Valid barcodes | 96.80% to 96.90% | 96.80% to 97% |
| Reads mapped to transcriptome | 47.40% to 48.20% | 47.20% to 49.10% |
| cDNA PCR duplication (20 k raw reads/cell) | 66.50% to 69.00% | 67.60% to 69.80% |
| Fraction Reads in cells | 95.10% to 95.80% | 95.10% to 95.90% |
| Median Genes/cell | 1155 to 1229 | 1102 to 1247 |
| Total Genes detected | 16397 to 16749 | 16351 to 16875 |
| Median UMI Counts per cell | 2827 to 3014 | 2553 to 3000 |
| Median genes per cell (20 k raw reads/cell) | 1053 to 1081 | 1019 to 1094 |
| Median UMI counts per cell (20 k raw reads/cell | 2519 to 2631 | 2357 to 2592 |

Table 2B summarizes the cell expression measurements and results for Samples 9-14.

TABLE 2B

| Measurement | Samples 9-10 | Samples 11-14 |
| --- | --- | --- |
| Estimated # of cells | 945 to 981 | 965 to 1063 |
| Mean reads/cell | 44253 to 72375 | 34001 to 39893 |
| Valid barcodes | 96.50% to 96.70% | 96.50% to 96.70% |
| Reads mapped to transcriptome | 61.60% to 62.30% | 61.70% to 61.90% |
| cDNA PCR duplication (20 k raw reads/cell) | 63.60% to 64.80% | 62.90% to 64.40% |
| Fraction Reads in cells | 94.90% | 94.20% to 94.70% |
| Median Genes/cell | 1359 to 1459 | 1297 to 1379 |
| Total Genes detected | 15,860 to 16295 | 15778 to 16087 |
| Median UMI Counts per cell | 4301 to 4726 | 4097 to 4449 |
| Median genes per cell (20 k raw reads/cell) | 1206 to 1247 | 1178 to 1227 |
| Median UMI counts per cell (20 k raw reads/cell | 3796 to 3956 | 3706 to 3923 |

Table 3A summarizes the cell surface protein measurement results for Samples 1-8.

TABLE 3A

| Measurement | Samples 15-18 | Samples 19-22 |
| --- | --- | --- |
| Q30 Bases in Antibody Read | 63.50% to 64.30% | 62.00% to 63.90% |
| Valid Barcodes | 98.50% to 98.50% | 98.50% to 98.50% |
| Valid UMIs | 100.00% to 100.00% | 100.00% to 100.00% |
| Fraction Antibody Reads | 78.60% to 79.00% | 76.70% to 78.10% |
| Fraction Antibody Reads Usable | 54.40% to 56.10% | 15.20% to 46.90% |
| Fraction Antibody Reads Usable per Cell | 6136 to 8277 | 1916 to 5881 |
| Antibody Reads in Cells | 74.20% to 75.30% | 21.50% to 65.20% |
| Median UMIs per cell at 1 k Antibody Reads Usable per cell | 640 to 678 | 391 to 663 |
| Median UMIs per Cell at 5 k Antibody Reads Usable per Cell | 1381 to 1511 | 1286 to 1436 |

Table 3B summarizes the cell surface protein measurement results for Samples 9-14.

TABLE 3B

| Measurement | Samples 23-24 | Samples 25-28 |
| --- | --- | --- |
| Q30 Bases in Antibody Read | 58.70% to 59.20% | 58.70% to 59.60% |
| Valid Barcodes | 98.80% to 98.80% | 98.80% to 98.90% |
| Valid UMIs | 100.00% to 100.00% | 100.00% to 100.00% |
| Fraction Antibody Reads | 97.10% to 97.10% | 96.90% to 97.20% |
| Fraction Antibody Reads Usable | 65.00% to 66.80% | 68.20% to 69.80% |
| Fraction Antibody Reads Usable per Cell | 12991 to 13796 | 13726 to 21064 |

TABLE 3B-continued

| Measurement | Samples 23-24 | Samples 25-28 |
|---|---|---|
| Antibody Reads in Cells | 67.70% to 69.60% | 71.10% to 72.70% |
| Median UMIs per cell at 1 k Antibody Reads Usable per cell | 677 to 678 | 679 to 721 |
| Median UMIs per Cell at 5 k Antibody Reads Usable per Cell | 1472 to 1540 | 1740 to 1796 |

The mass transport of DTT into GEMs after their generation had no negative impact on the ability to the measure gene expression profile of cells or to profile cell surface proteins. Samples 1-8 had disulfide conjugation chemistry between the antibody and nucleic acid barcode molecules and the DTT was provided in the RT Master Mix at four different concentrations (1 to 4 with 1 being the highest and 4 being the lowest concentration). The DTT concentrations fell within a range of 0.5 mM to 500 mM. Samples 9-14 had disulfide conjugation chemistry between the antibody and nucleic acid barcode molecules and the DTT was provided as oil or emulsion rather than in the RT Master mix.

Example 3: Sample Processing in Droplets Formed by Agitation

FIGS. 16A through 16E demonstrate an example workflow for processing analyte carriers. Referring to FIG. 16A, the method may comprise transposition of nuclei in bulk 1601. Referring to FIG. 16B, transposed nuclei 1602, one or more reagents, such as biochemical reagents 1603, and beads, such as barcoded gel beads 1604, may be added to a container, such as a tube 1605. The contents of the container may comprise the first fluid 1606. In some cases, excess aqueous liquid may be removed from the container, for example, using a pipette. The second fluid may be added to the container. The second fluid may comprise oil and surfactant. The container may be vortexed 1607. Droplets 1608 may be generated in the container. Beads may limit droplet break-up into droplets smaller than the size of the beads which may contribute to the monodispersity of the generated droplets. Droplets 1608 may comprise the beads, such as barcoded gel beads 1609 or the analyte carriers, such as transposed nuclei 1610, and/or both, such as illustrated in FIG. 16C. A droplet may comprise a single bead. A droplet may comprise a single analyte carrier. A droplet (e.g., 1613) may comprise a single bead and a single analyte carrier. One or more reagents 1611 may be transported 1612 into the droplets (e.g., 1613), such as illustrated in FIG. 16D. Transporting 1612 the reagent(s) into the droplets may be performed with the aid of a mediator, such as a micelle. Reagent(s) 1611 may comprise DTT. Reagent(s) may dissolve and/or degrade the beads, thereby generating a droplet 1614 comprising an analyte carrier in which the bead is dissolved. In some cases, the reagent(s) may release nucleic acid barcode molecules from the bead, such as by cleaving a bond. In some cases, the nucleic acid barcode molecules may be released into the droplet upon bead degradation. Thus, nucleic acid barcode molecules and an analyte carrier (e.g., transposed nucleus) may be co-partitioned in the droplet 1614. The method may further comprise processing the partitioned samples, such as generating barcoded products. For example, a nucleic acid barcode molecule and a nucleic acid molecule derived from an analyte carrier may be used to generate a barcoded product. In some cases, barcoded DNA fragments may be generated 1615 from a nucleic acid molecule derived from a transposed nucleus and a nucleic acid barcode molecule delivered on a bead. Samples may be further subjected to amplification reaction, such as PCR, such as linear amplification. Samples may be pooled. The second fluid (e.g., oil) may be removed 1616 from the container. The method may further comprise sequencing 1618. Generating droplets with the aid of agitation such as vortexing may contribute to the scalability of the process. For example, larger sample sizes may be processed without increasing workflow time. In some cases, biochemical processes may be scaled by a few to several orders of magnitude, without increasing workflow time.

Example 4: Single Cell Gene Expression in Droplets Formed by Agitation

FIGS. 17A through 17D demonstrate an example workflow for single cell gene expression, wherein droplets are generated with the aid of agitation. Referring to FIG. 17A, analyte carriers, such as cells 1701, one or more reagents, such as biochemical reagents 1702, and beads, such as gel beads, such as barcoded gel beads 1703 may be added to a container, such as a tube. The container may comprise the first fluid 1705. The first fluid 1705 may be an aqueous solution comprising analyte carriers (e.g., cells), reagent(s), and beads (e.g., barcoded gel beads), and in some cases, excess aqueous liquid. Excess aqueous liquid may be removed from the container. The second fluid comprising oil may be added to the container. Surfactant may be further added to the container. The container may be agitated (e.g., vortexed), such as illustrated in FIG. 17B. A droplet population may be generated by agitation. Beads may act as templates to form a monodispersed droplet population. A droplet 1707 in the droplet population may comprise a single bead 1708 and a single analyte carrier 1709, such as a single cell. Some droplets in the droplet population may comprise a single bead. Some droplets may not comprise any beads. Some droplets may comprise more than one bead. Some droplets may comprise an analyte carrier. Some droplets may not comprise any analyte carrier. Some droplet may comprise more than one analyte carrier. The analyte carrier may be a cell. Some droplets may comprise a single cell. Some droplets (e.g., droplet 1707) may comprise a single bead and a single cell. Droplets comprising a single cell and a single bead may be preferred for downstream operations. Referring to FIG. 17C, one or more reagents 1710 and 1711, such as biochemical reagents may be transported to the droplets. Reagents may be transported 1712 to the droplet from other droplets with the aid of a mediator, such as micelle. In some cases, reagents may comprise dithiothreitol (DTT) and n-dodecyl-beta-D-maltoside (DBDM). DTT may dissolve the gel beads. DBDM may lyse the cells. The reagents may otherwise release a nucleic acid barcode molecule from a bead and/or release a nucleic acid molecule derived from an analyte carrier in the droplet. Gel beads may comprise barcoded beads. As such, barcode molecules may be released into the droplet. Cell contents, such as intracellular contents, nucleic acid molecules, proteins, and/or cytoplasm, may be released into the droplet. Thus, subsequent to reagent transportation, some droplets 1713 may comprise barcode molecules and cell contents (lysed cells). The method may further comprise processing the partitioned samples, such as generating barcoded products (e.g., barcoded analyte carriers or barcoded analytes derived from the analyte carriers). For example, the bead may comprise a nucleic acid barcode molecule coupled thereto. The nucleic acid barcode molecule may be used to barcode an analyte carrier in the partition, or an analyte derived from the analyte carrier. In some cases, barcoded cDNA molecules may be generated. Samples may be further subjected to amplification reactions, such as PCR, such as linear amplification. Samples may be pooled. The second fluid (e.g., oil) may be removed from the container. The method may further comprise sequencing. Generating droplets with the aid of agitation such as vortexing may contribute to the scalability of the process. For example, larger sample sizes may be processed without increasing workflow time. In some cases, biochemical processes may be scaled by few to several orders of magnitude. Scaling may be achieved without increasing workflow time.

Example 5: Addition of Reagent after Droplet Generation

FIGS. 18A and 18B show the results of an experiment where transporting a lysis agent to a population of droplets comprising cells, such as single cells, can lyse the cells to release their contents into the interior of the droplets. FIG. 18A shows a population of droplets in a container (e.g., the second droplet population) 1801 in which cells are encapsulated. A brightfield microscopy image 1802 and a fluorescent microscopy image 1803 show the droplets, some of which comprise cells. Some droplets may be empty. Some droplets may comprise single cells. Some droplets may comprise multiple cells. In some cases, droplets may comprise one or more beads and/or one or more cells. In some cases, some droplets may comprise a single cell and a single bead. Cells may be fluorescent cells. Cells may be stained by a fluorescent dye, such as Calcein, or other fluorescent dyes. Fluorescent dyes may be visualized using an appropriate light filter on the microscope to allow visualization at a certain wavelength. Cells may be intact. Intact, unlysed cells may appear as puncta on the fluorescent image 1803. Referring to FIG. 18B, one container may comprise a population of droplets 1804 (e.g., second droplet population) which may comprise cells and beads. Another container may comprise a population of droplets 1805 (e.g., the first droplet population). The first and second droplet populations 1804 and 1805 may be mixed. A droplet in the first droplet population 1805 may comprise a reagent. The reagent may comprise a lysis agent. The reagent may comprise n-dodecyl-beta-D-maltoside (DBDM). Lysis agents can be transported into the second droplet population such as shown in brightfield 1806 and fluorescent 1807 microscopy images in FIG. 18B. The reagent can lyse the cell inside the droplet. Cell lysis inside the droplet may result in diffusion of the fluorescent dye/stain such as Calcein stain throughout the droplet rendering the cell-containing droplets fluorescent (see image 1807). Some droplets may not be rendered fluorescent. Such droplets are suspected of not having cells in them.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for nucleic acid processing, comprising:
   (a) generating a plurality of droplets by agitating:
      (i) a first fluid volume comprising a population of beads and a population of analyte carriers, wherein a bead of the population of beads comprises a plurality of nucleic acid barcode molecules, and wherein an analyte carrier of the population of analyte carriers comprises a plurality of nucleic acid molecules, and
      (ii) a second fluid volume immiscible with the first fluid volume,
      wherein a first droplet of the plurality of droplets comprises the bead of the population of beads and the analyte carrier of the population of analyte carriers;
   (b) subjecting the first droplet and a second droplet comprising a reagent to conditions sufficient to transfer the reagent to the first droplet from the second droplet via a mediator comprising an aggregate of surfactant molecules and the reagent, wherein the reagent is configured to release the plurality of nucleic acid molecules from the analyte carrier; and
   (c) generating a barcoded nucleic acid molecule using a nucleic acid barcode molecule of the plurality of nucleic acid barcode molecules and a nucleic acid molecule of the plurality of nucleic acid molecules.

2. The method of claim 1, wherein the population of analyte carriers is a population of cells or nuclei, and wherein the analyte carrier is a cell or a nucleus.

3. The method of claim 2, wherein the reagent is a lysis agent.

4. The method of claim 3, wherein the method comprises lysing the cell or the nucleus with the lysis agent in the first droplet.

5. The method of claim 4, wherein the lysis agent is a surfactant.

6. The method of claim 4, wherein the lysis agent is n-dodecyl-beta-D-maltoside (DBDM), sodium lauroyl sarcosinate, sodium dodecyl sulfate (SDS), t-Octylphenoxypolyethoxyethanol, or polysorbate 20.

7. The method of claim 4, wherein the lysis agent is an enzyme.

8. The method of claim 1, wherein the nucleic acid molecule is a messenger ribonucleic acid (mRNA).

9. The method of claim 8, wherein the nucleic acid barcode molecule hybridizes to the mRNA.

10. The method of claim 9, wherein generating the barcoded nucleic acid molecule comprises extending the nucleic acid barcode molecule in a reverse transcription reaction using the mRNA as template.

11. The method of claim 10, wherein the method further comprises sequencing the barcoded nucleic acid molecule or a derivative thereof.

12. The method of claim 1, wherein the mediator is a micelle.

13. The method of claim 1, wherein the aggregate of surfactant molecules comprises a fluorosurfactant.

14. The method of claim 1, wherein the second fluid volume comprises oil.

15. The method of claim 14, wherein the oil is a fluorinated oil and the second fluid volume further comprises a fluorosurfactant.

16. The method of claim 1, wherein the plurality of droplets comprises monodisperse droplets.

17. The method of claim 1, wherein the agitating comprises vortexing.

18. The method of claim 1, wherein the plurality of droplets is a first plurality of droplets, wherein the second droplet is a second droplet of a second plurality of droplets comprising the reagent, and wherein (b) comprises subjecting the first plurality of droplets and the second plurality of droplets to the conditions sufficient to transfer the reagent to the first droplet from the second droplet.

19. The method of claim 18, wherein (b) comprises contacting the first plurality of droplets with the second plurality of droplets.

20. The method of claim 19, wherein the first plurality of droplets is formed in a first emulsion, the second plurality of droplets is formed in a second emulsion, and wherein (b) comprises contacting the first emulsion with the second emulsion.

21. The method of claim 1, wherein the population of analyte carriers is a population of cells or nuclei, and wherein the mediator is a micelle.

* * * * *